(12) United States Patent
Murata

(10) Patent No.: US 9,372,336 B2
(45) Date of Patent: Jun. 21, 2016

(54) ENDOSCOPE OBJECTIVE OPTICAL SYSTEM

(71) Applicant: Olympus Corporation, Tokyo (JP)

(72) Inventor: Keiji Murata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/100,257

(22) Filed: Dec. 9, 2013

(65) Prior Publication Data

US 2014/0155694 A1 Jun. 5, 2014

Related U.S. Application Data

(63) Continuation of application No. PCT/JP2013/062832, filed on May 7, 2013.

(30) Foreign Application Priority Data

Jul. 3, 2012 (JP) ................................. 2012-149750

(51) Int. Cl.
*A61B 1/04* (2006.01)
*G02B 23/24* (2006.01)
*A61B 1/00* (2006.01)
*A61B 1/055* (2006.01)

(52) U.S. Cl.
CPC ........ *G02B 23/2407* (2013.01); *A61B 1/00096* (2013.01); *A61B 1/00197* (2013.01); *A61B 1/055* (2013.01); *G02B 23/243* (2013.01)

(58) Field of Classification Search
CPC ............. G02B 23/2407; G02B 23/243; A61B 1/00096

USPC .................. 359/656–661; 600/109, 160, 177; 348/340

See application file for complete search history.

(56) References Cited

U.S. PATENT DOCUMENTS 3,647,282 A * 3/1972 Taira ............................. 359/661
3,744,881 A * 7/1973 Taira ............................. 359/659

(Continued)

FOREIGN PATENT DOCUMENTS

JP  56-086513   5/1983
JP  2740662    4/1998

(Continued)

OTHER PUBLICATIONS

International Search Report, mailed Aug. 13, 2013, issued in corresponding International Application No. PCT/JP2013/062832.

(Continued)

*Primary Examiner* — Anhtuan T Nguyen
*Assistant Examiner* — Jae Woo
(74) *Attorney, Agent, or Firm* — Kenyon & Kenyon LLP

(57) ABSTRACT

Provided is an endoscope objective optical system including, in order from an object side, an aperture stop, a front group having positive refractive power, and a rear group having positive refractive power, in which the rear group is formed by joining a single lens having positive refractive power and a single lens having negative refractive power and is joined to an imaging device; a joining surface between the single lenses has positive refractive power; and the endoscope objective optical system satisfies following Conditional Expression (1):

$$0.15 < fF/fR < 0.5, \qquad (1)$$

where fF indicates a focal length of the front group, and fR indicates a focal length of the rear group.

14 Claims, 26 Drawing Sheets

(56) References Cited

U.S. PATENT DOCUMENTS

| | | | |
|---|---|---|---|
| 4,037,938 A | 7/1977 | Yamashita et al. | |
| 4,042,295 A * | 8/1977 | Yamasita et al. | 359/735 |
| 4,279,477 A * | 7/1981 | Tojo | 359/660 |
| 4,280,757 A * | 7/1981 | Tojo | 359/660 |
| 4,588,264 A * | 5/1986 | Shimizu | 359/657 |
| 4,664,486 A * | 5/1987 | Landre et al. | 359/380 |
| 4,721,372 A | 1/1988 | Yokota | |
| 4,753,224 A * | 6/1988 | Tojo | 356/241.5 |
| 4,867,136 A * | 9/1989 | Suzuki et al. | 600/109 |
| 4,979,808 A * | 12/1990 | Yamagata et al. | 359/740 |
| 4,986,642 A * | 1/1991 | Yokota et al. | 359/708 |
| 5,059,005 A * | 10/1991 | Kawano | 359/654 |
| 5,175,652 A * | 12/1992 | Shimizu | 359/793 |
| 5,198,931 A * | 3/1993 | Igarashi | 359/660 |
| 5,530,591 A * | 6/1996 | Tachihara et al. | 359/661 |
| 5,547,457 A * | 8/1996 | Tsuyuki et al. | 600/175 |
| 5,579,174 A * | 11/1996 | Tachihara et al. | 359/784 |
| 5,729,390 A * | 3/1998 | Abe | 359/661 |
| 5,777,797 A * | 7/1998 | Miyano | 359/660 |
| H1763 H * | 12/1998 | Mizusawa | 359/656 |
| 5,852,515 A * | 12/1998 | Kurata | 359/660 |
| 5,889,618 A * | 3/1999 | Fukutake | 359/661 |
| 5,916,148 A * | 6/1999 | Tsuyuki | 600/176 |
| 5,936,778 A * | 8/1999 | Miyano et al. | 359/660 |
| 5,940,220 A * | 8/1999 | Suenaga et al. | 359/660 |
| 5,961,445 A * | 10/1999 | Chikama | 600/112 |
| 6,128,139 A * | 10/2000 | Fukutake | 359/661 |
| 6,206,825 B1 * | 3/2001 | Tsuyuki | 600/182 |
| 6,252,723 B1 * | 6/2001 | Nagaoka | 359/689 |
| 6,476,851 B1 * | 11/2002 | Nakamura | 348/65 |
| 6,554,767 B2 * | 4/2003 | Tanaka | 600/175 |
| 6,844,985 B2 * | 1/2005 | Murayama | 359/686 |
| 6,855,110 B2 * | 2/2005 | Igarashi | 600/166 |
| 7,046,450 B2 * | 5/2006 | Hirata | 359/657 |
| 7,160,249 B2 * | 1/2007 | Hasegawa | 600/167 |
| 7,177,088 B2 * | 2/2007 | Hirata | 359/659 |
| 7,215,478 B1 * | 5/2007 | Hirata | 359/656 |
| 7,267,647 B2 * | 9/2007 | Okada et al. | 600/166 |
| 7,502,182 B2 * | 3/2009 | Miyano | 359/793 |
| 7,789,823 B2 * | 9/2010 | Kato et al. | 600/109 |
| 7,796,342 B2 * | 9/2010 | Baba | 359/648 |
| 7,828,721 B2 * | 11/2010 | Kumei et al. | 600/109 |
| 7,929,219 B2 * | 4/2011 | Togino | 359/736 |
| 8,118,734 B2 * | 2/2012 | Murayama | 600/177 |
| 8,164,836 B2 * | 4/2012 | Uzawa et al. | 359/690 |
| 8,164,839 B2 * | 4/2012 | Nasu | 359/783 |
| 8,243,129 B2 * | 8/2012 | Uzawa | 348/65 |
| 8,314,835 B2 * | 11/2012 | Kanzaki et al. | 348/75 |
| 8,366,609 B2 * | 2/2013 | Iwasaki et al. | 600/168 |
| 8,441,529 B2 * | 5/2013 | Sasamoto | 348/65 |
| 8,477,436 B2 * | 7/2013 | Sasamoto | 359/793 |
| 8,542,444 B2 * | 9/2013 | Baba et al. | 359/642 |
| 8,721,531 B2 * | 5/2014 | Ichimura et al. | 600/169 |
| 2004/0190159 A1 | 9/2004 | Hasegawa | |
| 2007/0010711 A1 * | 1/2007 | Hasegawa | 600/168 |
| 2008/0080061 A1 * | 4/2008 | Miyano | 359/661 |

FOREIGN PATENT DOCUMENTS

| | | |
|---|---|---|
| JP | 10-115776 | 5/1998 |
| JP | 2000-019390 | 1/2000 |
| JP | 2002-365535 | 12/2002 |
| JP | 3450543 | 9/2003 |
| JP | 2004-088713 | 3/2004 |
| JP | 2004-163986 | 6/2004 |
| JP | 2007-159836 | 6/2007 |
| JP | 4245800 | 4/2009 |
| JP | 2009-294494 | 12/2009 |
| JP | 4732480 | 7/2011 |
| WO | 2011/033513 | 3/2011 |

OTHER PUBLICATIONS

European Extended Search Report, dated Feb. 19, 2016, issued in corresponding European Patent Application No. 13812701.4.

* cited by examiner

ENDOSCOPE OBJECTIVE OPTICAL SYSTEM

CROSS-REFERENCE TO RELATED APPLICATIONS

This is a continuation of International Application PCT/JP2013/062832, with an international filing date of May 7, 2013, which is hereby incorporated by reference herein in its entirety. This application claims the benefit of Japanese Patent Application No. 2012-149750, the content of which is incorporated herein by reference.

TECHNICAL FIELD

The present invention relates to a very small endoscope objective optical system.

BACKGROUND ART

Compact optical systems that can observe a large area have been conventionally demanded as the objective optical systems for endoscopes. In order to realize such an optical system, it is necessary to reduce the entire length, the outer diameter, and the focal length. In particular, in an endoscope objective optical system used to observe thin lumen, such as the bronchi, the biliary tract, and the pancreatic duct, the most important thing is to reduce the diameter of the endoscope; therefore, optical systems for which a small diameter and short length are given priority over maintaining image quality and that consist of a few lenses have been adopted (for example, see PTLs 1 to 9).

As in PTLs 1 and 2, with a so-called retrofocus-type optical system in which a concave lens is disposed at the front end, a wider angle can be realized relatively easily. The above-described concave lens is formed into a meniscus shape or a plano-concave shape provided with a surface having a large refractive power on the image side and thus needs to ensure an increased thickness. Furthermore, in general, in the retrofocus-type optical system, the diameter of a front lens tends to increase.

In ultrasmall-diameter endoscopes, lenses whose outer diameters are 1 mm or smaller are often used. The lens processing becomes more difficult as the lens diameters are reduced, as well as the accurate processing is required for frames having a thickness of about 0.1 mm. Usually, lenses are held with a simply-structured frame, such as that shown in FIG. 13 or FIG. 15 of PTL 3, for example, and it is difficult to process a frame that has many step portions and that is formed by combining a plurality of members, such as that shown in FIG. 1 of PTL 4. From this view point, a configuration in which a concave lens is provided as the front lens is undesirable.

On the other hand, as a lens configuration for realizing a wide angle while being small in size, a configuration consisting of a stop, a front group having positive refractive power, and a rear group having positive refractive power is known (for example, see PTLs 5 and 6). This lens configuration has the advantage that the optical system can be reduced in length and diameter. However, as in PTL 6, for example, if lenses are disposed away from an imaging device, the number of places where air spaces are required increases, thus tending to increase the length of the optical system. Furthermore, in an oblique-incidence imaging device, because a convex lens is disposed at a position where the ray height is high, a sufficient distortion effect cannot be obtained, thus making it difficult to realize a wider angle. If one attempts to realize this by increasing the refractive power of the rear group, the curvature needs to be increased, thus deteriorating the ease-of-processing, and in that a sufficient edge thickness cannot be ensured, thus deteriorating the ease-of-handling. Therefore, in order to realize both ease-of-processing and a wide angle, it is preferable that the rear group having positive refractive power be disposed near the imaging device.

In addition, if the imaging device is a solid-state imaging device, a cover glass located on the surface thereof is not round in many cases; thus, a member serving as a guide for aligning the center of the imaging area with the center of the objective optical system is provided, and other members are mated with this member for alignment, thereby facilitating assembly (for example, see PTL 3). For this purpose, a flat glass or a plano convex lens attached directly on top of the imaging device is generally used. In contrast, in the case of the above-described lens configuration consisting of the stop, the front group having positive refractive power, and the rear group having positive refractive power, when the rear group having positive refractive power is made to serve as this guide, this is advantageous in terms of a reduction in size of the optical system.

From these circumstances, in order to realize both a reduction in size and a wider angle, as in PTLs 3 and 7, it is preferable to provide an optical system that adopts the lens configuration consisting of the stop, the front group having positive refractive power, and the rear group having positive refractive power and in which the lens group having positive refractive power in the rear group is joined to the imaging device.

In such an optical system, when strong light enters from outside the visual field, a ray striking an inner circumferential surface of a portion of a frame between air surfaces located between the front group and the rear group is reflected, thus tending to cause flare. For example, when performing ray tracing in a frame structure estimated from the drawings of PTL 3, it is confirmed that flare occurs, as shown in FIG. 24. In the figure, reference symbol GF denotes the front group, reference symbol GR denotes the rear group, reference numeral 1 denotes a frame for holding lenses in the front group, reference numeral 2 denotes a frame for holding a lens in the rear group, reference numeral 10 denotes a cover glass, and reference numeral 11 denotes a sealing glass provided on an imaging surface of the imaging device. Such flare occurs near the center of the visual field over a wide range.

Of course such flare can be prevented by increasing the lens diameter of the rear group to keep the inner circumferential surface of the frame far from the optical axis. However, the diameter of the optical system would be increased, the diameter of the lens in the rear group having positive refractive power, to be mated with the frame, would need to be increased, and the edge thickness of the lens would be reduced, thus deteriorating the ease-of-processing and ease-of-assembly.

Thus, in PTL 8, the rear group having positive refractive power is formed of a joined lens, and the joined lens is joined to an end surface of the imaging device, thereby inhibiting flare caused by light reflected at the inner circumferential surface of the frame. PTL 8 is based on the technological idea that a ring serving as the frame is omitted to accordingly increase the inner diameter of the frame, and a sufficient distance between the optical axis and the inner circumferential surface of the frame is not ensured; therefore, when a ray enters from outside the visual field, flare still occurs. This is clear from the fact that, in the ray diagram of FIG. 5 in PTL 8, a ray that does not reach the outermost off-axis position passes through a place close to the inner circumferential surface of the frame.

Furthermore, flare can be inhibited from occurring by changing the frame shape through light-blocking processing applied to the frame for a camera lens. However, from the above-described circumstances, it is difficult to apply such processing to a very small frame in an endoscope optical system, and accuracy is required, thus leading to a large increase in cost.

Similarly, a method in which a light-blocking member, such as a flare diaphragm, is disposed in the optical path can be considered. In order to realize this configuration by using a mask member, for example, because the optical system is very small, the light-blocking member itself has to be very small and very thin. Furthermore, it is necessary to provide the frame with a receiving portion to which the mask member is fixed, which inevitably makes frame processing more and more difficult, and a ray can strike the light-blocking member itself, causing even stronger flare depending on how surface treatment is done. In addition, when the mask member is fixed by bonding, because the bonding area is reduced due to a reduction in size, the fixing strength is very weak, thus making it easy for the mask member to peel off.

While there are limits to inhibiting flare by using a mechanical member, as described above, PTL 9 proposes a technology for reducing the occurrence of flare by providing the lens in the rear group with an inclined portion. PTL 9 is based on the premise that light strikes the inner circumferential surface of the frame; therefore, the amount of stray light that can be cut differs depending on the size of the inclined portion, and the intensity of flare changes significantly.

In particular, in the optical system for an ultrathin endoscope, because the lens itself for which the inclined portion is provided is small, small variations in the size of the inclined portion determine the intensity of flare, which makes it impossible to stably inhibit the occurrence of flare. Even when a sufficient size of the inclined portion is ensured in order to solve this problem, the inclined portion overlaps an area for necessary rays, thus reducing peripheral performance because of loss of light due to vignetting. Furthermore, the mating area where the lens in the rear group is mated with the frame is reduced, thus reducing the strength of the imaging unit.

CITATION LIST

Patent Literature

{PTL 1}
 Japanese Unexamined Patent Application, Publication No. 2002-365535
{PTL 2}
 The Publication of Japanese Patent No. 3450543
{PTL 3}
 Japanese Unexamined Patent Application, Publication No. 2009-294494
{PTL 4}
 Japanese Unexamined Patent Application, Publication No. 2007-159836
{PTL 5}
 The Publication of Japanese Patent No. 4245800
{PTL 6}
 The Publication of Japanese Patent No. 4732480
{PTL 7}
 The Publication of Japanese Patent No. 2740662
{PTL 8}
 Japanese Unexamined Patent Application, Publication No. Sho 58-86513
{PTL 9}
 Japanese Unexamined Patent Application, Publication No. 2000-19390

SUMMARY OF INVENTION

The present invention provides an endoscope objective optical system including, in order from an object side: an aperture stop; a front group having positive refractive power; and a rear group having positive refractive power, in which the rear group is formed by joining a single lens having positive refractive power and a single lens having negative refractive power and is joined to an imaging device; a joining surface between the single lenses has positive refractive power; and the endoscope objective optical system satisfies following Conditional Expression (1):

$$0.15 < fF/fR < 0.5, \tag{1}$$

where fF indicates a focal length of the front group, and fR indicates a focal length of the rear group.

DESCRIPTION OF EMBODIMENTS

An endoscope objective optical system (hereinafter, simply referred to as objective optical system) 100 according to one embodiment of the present invention will be described below with reference to FIG. 1.

Figure 1:
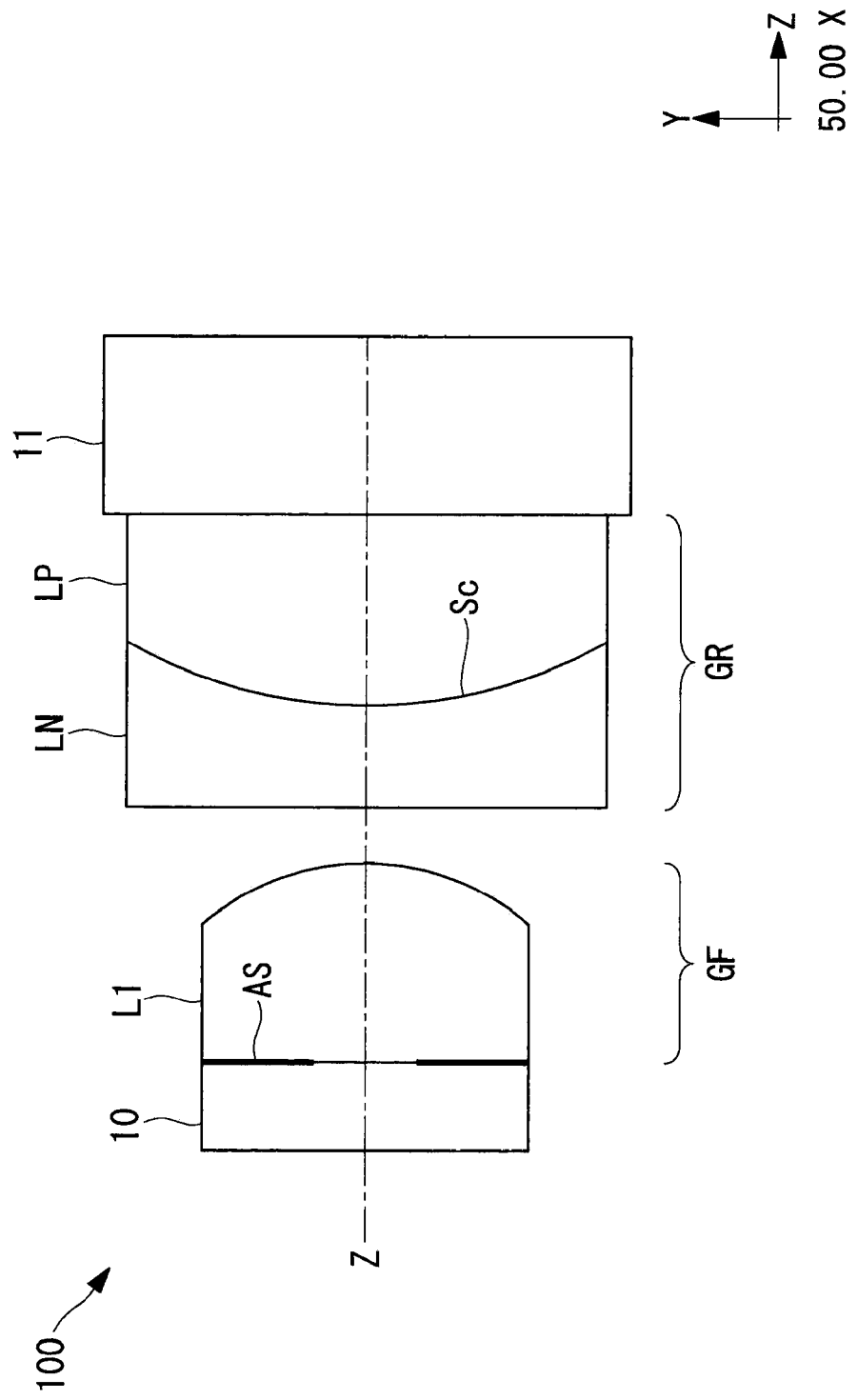
FIG. 1 is a lens cross-sectional view showing the configuration of an endoscope objective optical system according to one embodiment of the present invention.

As shown in FIG. 1, the objective optical system 100 of this embodiment consists of, in order from an object side, an aperture stop AS that is formed on one surface of a cover glass 10, a front group GF having positive refractive power, and a rear group GR having positive refractive power.

The aperture stop AS is formed by evaporating a light-blocking material on a circumferential portion of the image-side surface of the cover glass 10.

The front group GF is formed of one positive lens L1.

The rear group GR is formed of a joined lens that is formed by joining a single lens LN having negative refractive power, and the a single lens LP having positive refractive power, and a joining surface Sc between the single lenses LN and LP has positive refractive power. Furthermore, the rear group GR is joined to an imaging device (not shown) via a sealing glass 11.

Reference symbol Z in the figure indicates an optical axis of the objective optical system 100.

The objective optical system 100 satisfies the following Conditional Expressions (1) to (5):

$$0.15 < fF/fR < 0.5; \tag{1}$$

$$0.4 < \Phi c \cdot fR < 1.8; \tag{2}$$

$$2.0 < L/f < 3.4; \tag{3}$$

$$0.707 < Ih/f < 0.956; \text{ and} \tag{4}$$

$$Hm < DR/2, \tag{5}$$

where fF indicates the focal length of the front group GF; fR indicates the focal length of the rear group GR; $\Phi c$ indicates the refractive power of the joining surface Sc between the single lens LP, which has positive refractive power, and the single lens LN, which has negative refractive power, of the rear group GR; f indicates the focal length of the entire objective optical system 100; L indicates the entire length from a front end to a rear end of the objective optical system 100; Ih indicates the maximum image height on the imaging device; Hm indicates the height of an outermost off-axis chief ray at a refractive surface of the rear group GR that is closest to the object; and DR indicates the maximum outer diameter of the rear group GR.

Here, when the joining surface Sc has positive refractive power, this means that, in a case in which a glass material having refractive index N and a glass material having refractive index N' are joined, in order from an object side, at a surface having the radius of curvature r (here, positive when the center of curvature is located at the object side), the refractive power of the surface, which is defined by $\Phi=(N'-N)/r$, is positive. As long as this conditional expression is satisfied, the rear group GR may consist of a positive single lens LP and a negative single lens LN, in this order from the object side, or may consist of a negative single lens LN and a positive single lens LP, in this order from the object side.

The endoscope objective optical system 100 of this embodiment has a simply-structured frame, while being small in size and diameter and allowing a wide angle of view, and is designed to inhibit the occurrence of flare by reducing the height of an off-axis ray entering the rear group GR having positive refractive power, thus eliminating reflection at the inner circumferential surface of the frame.

As described earlier, when the rear group GR is joined to the imaging device, the rear group GR serves as a guide to facilitate alignment of the centers of the endoscope objective optical system 100 and the imaging device, and a reduction in size can be realized. On the other hand, when the rear group GR having positive refractive power is configured such that a single lens LP having positive refractive power and a single lens LN having negative refractive power are joined, and the joining surface Sc therebetween has positive refractive power, the rear group GR of the optical system of this embodiment has positive refractive power as a whole, and a ray entering the imaging device is subjected to a convergence effect twice. The reason why flare is inhibited by this configuration will be described below.

First, the imaging device has incidence characteristics within a certain angular range, regardless of whether the imaging device is a solid-state imaging device, such as a CCD or a CMOS device, or a device like an image guide fiber. It is known that, if rays enter from outside this certain angular range, a detrimental effect (shading) is exerted on observation; for example, the circumferential portion of an image becomes dark, or the circumferential portion thereof appears to be colored. In short, the position of the exit pupil cannot be set as desired but needs to be fixedly set for each imaging device. When this point is taken into account, it is clear that, by configuring the rear group GR such that a ray is subjected to the convergence effect twice in the rear group GR, it is possible to maintain the incidence characteristics and the refractive power of the rear group GR at the surface of the rear group GR that is closest to the object and to set the ray height lower, compared with other configurations.

In this way, when the ray height at the surface of the rear group GR that is closest to the object is set low, a margin is produced between even an outermost off-axis ray and the inner circumferential surface of the frame, between air surfaces located between the front group GF and the rear group GR. This allows an optical system in which, even if an outermost off-axis ray, i.e., a ray having the maximum height at each lens surface, enters the optical system, flare caused when the ray is reflected at the inner circumferential surface of the frame does not occur.

Figure 5:
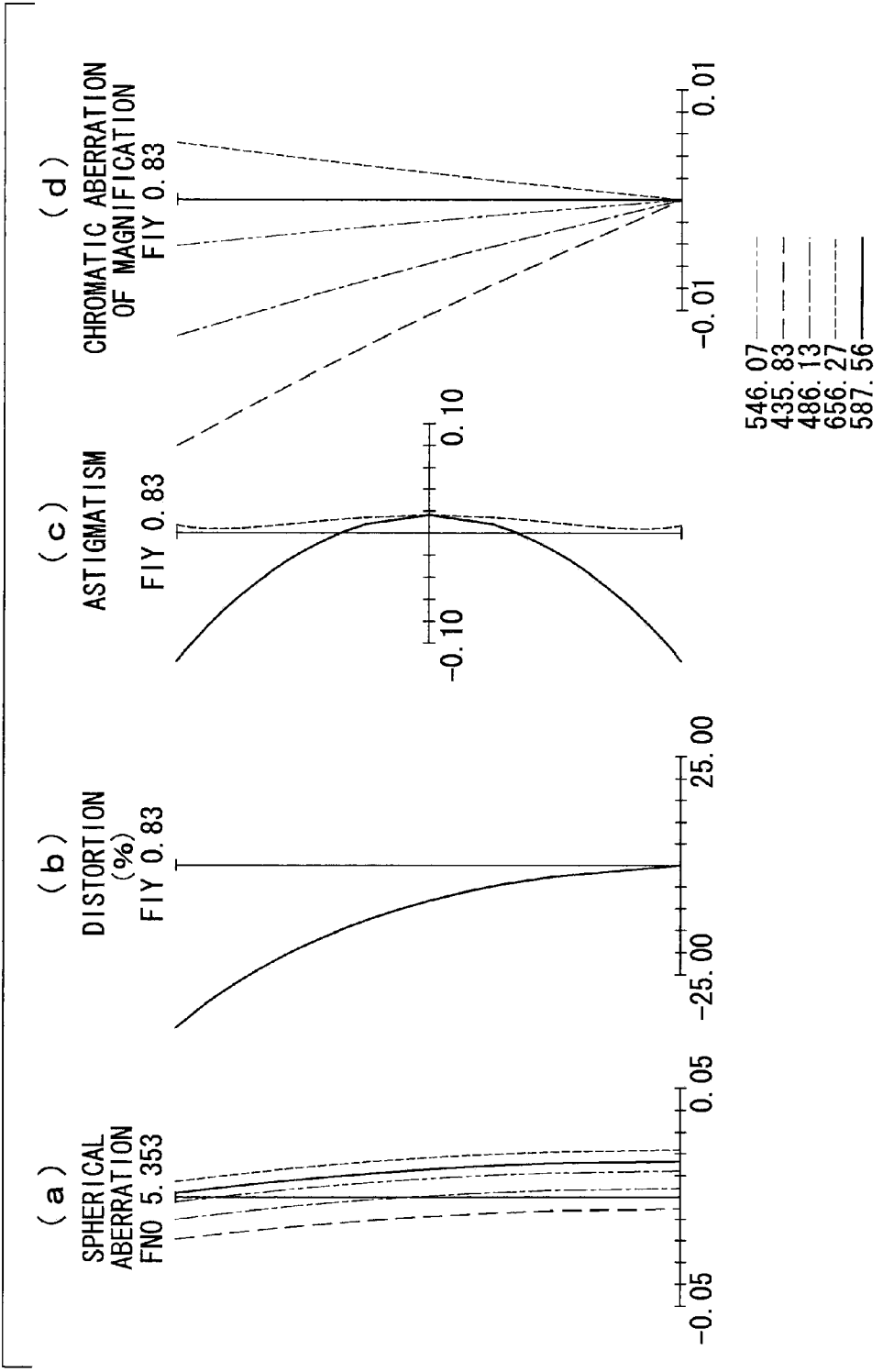
FIG. 5 includes aberration diagrams showing (a) spherical aberration, (b) distortion, (c) astigmatism, and (d) chromatic aberration of magnification of the endoscope objective optical system of Example 2.

Note that, although the joined lens is joined to the imaging device in the invention described in PTL 8, as well, PTL 8 differs from this embodiment in that the joining surface has negative refractive power in FIG. 5, which shows an Example that is the most similar to the configuration of this embodiment. If the joining surface having negative refractive power is adopted, because a ray is subjected to a diverging effect so as to go away from the optical axis, it is impossible to reduce the ray height at the surface of the rear group that is closest to the object while maintaining the incidence characteristics. It is clear from the figure of the Example that the ray height is high at the surface of the rear group that is closest to the object; therefore, flare still occurs. In this way, PTL 8 is not designed to inhibit flare by preventing reflection at the frame, unlike this embodiment.

Similarly, the invention disclosed in the Publication of Japanese Patent No. 3685278 adopts a configuration in which a joined lens is attached to an imaging device, so that there is no concept of the inner circumferential surface of the frame between the front group and the rear group; therefore, flare does not occur in the first place, and a reduction in size can be achieved. However, the lenses are joined, thus weakening the refractive power of the front group, which makes it impossible to achieve a wider angle. When a strong power is to be achieved at the surface closest to the object, the concentricity is lost, which causes astigmatism and significantly deteriorates the imaging performance; therefore, it is impossible to simultaneously achieve a reduction in size and diameter, a wider angle, and inhibition of the occurrence of flare. Furthermore, although a positive lens is made of a glass material having a refractive index higher than that for a negative lens, and each joining surface has positive refractive power, such a glass material is designed with the intention of reducing the Petzval sum and does not take into account the occurrence of flare.

Conditional Expression (1) expresses a condition that can realize a sufficient reduction in diameter in the lens configuration of this embodiment. Features of the above-described lens configuration consisting of the aperture stop, the front group GF having positive refractive power, and the rear group GR having positive refractive power include a structure in which the lens in the front group GF is disposed almost concentrically with the aperture stop. Specifically, by adopting a symmetric structure with respect to the center of the aperture stop, it is possible to inhibit comatic aberration and field curvature. Therefore, the size is reduced while maintaining the almost-concentric arrangement of the front group GF with respect to the aperture stop, thereby making it possible to reduce the outer diameter while successfully correcting aberrations and to reduce the entire length of the optical system.

From the above description, it is found that allocating refractive power to the front group GF is effective in reducing the size of the front group GF. If fF/fR is set to 0.15 or smaller, the radius of curvature and the diameter become too small, going beyond the limits of processing. If this problem is to be solved by using a high-refractive-index glass material, the concentricity is lost, thus causing comatic aberration. Furthermore, in general, a high-refractive-index glass material has a low Abbe number, thus causing chromatic aberration of magnification and significantly deteriorating the optical performance, which is not desirable.

On the other hand, if fF/fR is set to 0.5 or larger to allocate refractive power to the rear group GR, it is difficult to reduce the diameter of the front group GF, and the curvature of the rear group GR becomes steep, thus causing significant ray bending, significant comatic aberration, and astigmatism, which makes it impossible to obtain sufficient optical performance. Furthermore, in a case in which the lens in the rear group GR has a relatively large outer diameter, if the curvature becomes steep, sufficient edge thickness cannot be ensured; therefore, the thickness of the lens has to be increased, thus making it impossible to reduce the length of the optical system.

Next, as to Conditional Expression (2), $\Phi c \cdot fR$ indicates the proportion of the refractive power of the joining surface Sc in the rear group GR to the refractive power of the entire rear group GR. If $\Phi c \cdot fR$ is increased, the incidence angle at the imaging device is approximately parallel to the optical axis. Then, if $\Phi c \cdot fR$ is 1.8 or larger, an oblique-incidence optical system is provided in which rays incident on the imaging device at the maximum image height become parallel to the optical axis; that is to say, as the rays travel toward the image through an image-space telecentric, the rays approach the optical axis. An imaging device having such incidence characteristics is extremely rare for an endoscope for which a reduction in size is required. Furthermore, even if the imaging device had a certain range of incidence characteristics, it is important that the ray height at the surface of the rear group GR that is closest to the object be low in order to inhibit flare, and the above-described oblique-incidence characteristics are opposed to this requirement, which is not desirable.

On the other hand, if $\Phi c \cdot fR$ is small, the refractive power of the rear group GR is allocated to a surface other than the joining surface Sc, specifically, at the surface of the rear group GR that is closest to the object. In particular, if $\Phi c \cdot fR$ is 0.4 or smaller, because the refractive power of the joining surface Sc is reduced, and the radius of curvature of the surface of the rear group GR that is closest to the object has to be reduced, there is the same problem as the case in which the rear group GR is formed of a single lens LP having positive refractive power. Specifically, rays are likely to strike the inner circumferential surface of the frame, thus making it difficult to sufficiently inhibit the occurrence of flare.

Furthermore, when the rear group GR having positive refractive power consists of, in order from the object side, a single lens LN having negative refractive power and a single lens LP having positive refractive power, if $\Phi c \cdot fR$ is small, the shape of the single lens LN having negative refractive power approximates a meniscus shape in which the radii of curvature of both surfaces have values close to each other, including their signs. In general, it is difficult to accurately perform "center alignment" for aligning the center of the optical system with the center of the outer diameter of the meniscus-shaped lens during processing. On the other hand, if Φc·fR is large, the curvature of the joining surface Sc becomes steep, which deteriorates the ease-of-processing of the single lens LP having positive refractive power. In view of the ease-of-processing, in the above-described invention, it is more preferred that 0.7Φc·fR<1.45 be satisfied.

On the other hand, when the rear group GR having positive refractive power consists of, in order from the object side, a single lens LP having positive refractive power and a single lens LN having negative refractive power, if Φc·fR is reduced, a sufficient edge thickness of the single lens LP having positive refractive power cannot be ensured, thus significantly deteriorating the ease-of-processing. On the other hand, if Φc·fR is increased, the curvature of the joining surface Sc becomes steep, as described above, thus deteriorating the ease-of-processing of both the single lens having positive refractive power and the single lens LN having negative refractive power. Therefore, in view of the ease-of-processing, in the above-described invention, it is more preferred that 0.6<Φc·fR≤1 be satisfied.

In addition, because the surface joined to the imaging device is usually flat, if the surface of the rear group GR that is closest to the object is flat, specifically, if Φc·fR is 1, aberration does not occur at the surface of the rear group GR that is closest to the object, giving superior ease of lens processing, thus resulting in a particularly desirable configuration.

Conditional Expression (3) expresses a condition that can realize a sufficient reduction in the length of the entire optical system, in the lens configuration of this embodiment. If L/f is 2.0 or smaller, the lenses have to be extremely thin, which makes processing and assembling difficult. Furthermore, the combination of glass materials to be joined is limited because the refractive powers of the lenses need to be very strong, which makes it impossible to sufficiently correct the chromatic aberration of magnification.

On the other hand, if L/f is 3.4 or larger, even with a lens configuration in retrofocus-type optical systems, for example, a wider angle can be achieved while inhibiting the occurrence of flare. However, if L/f is smaller than 3.4, the frame structure can be made more simple than in such optical systems; therefore, this embodiment has a great advantage that both ease-of-processing and ease-of-assembly can be achieved.

Although it is better to reduce L/f to achieve a reduction in size, it is preferable that a flat cover made of glass or a crystal glass material, such as sapphire or spinel, having chemical resistance be disposed in front of the aperture stop. Thus, various types of resistance can be ensured. Furthermore, if a light-blocking area can be evaporated on a mirror surface of that cover, the aperture stop is formed on the mirror surface through evaporation, thereby making it possible to inhibit ray vignetting caused when the aperture stop has a thickness with respect to oblique-incidence rays and to effectively keep a peripheral visual field bright. Therefore, in view of the thickness of the cover, if 2.6<L/f<3.1 is satisfied, a reduction in size, a wider angle, resistance, and brightness of the peripheral visual field can be realized, which is more preferable.

In an ultrasmall-diameter endoscope, it is extremely difficult to distribute light widely to make the periphery bright. Therefore, it is necessary not only to achieve a wide angle but also to ensure brightness in the periphery at the same time. In view of such a circumstance, Conditional Expression (4) expresses a condition that can realize an optical system allowing a wide angle and a bright visual field, based on how distortion appears.

There are many ultrasmall-diameter endoscopes having field angles from about 90° to 120°, specifically, half field angles from about 45° to 60°. If Ih/f is larger than 0.707, this means that distortion of about f sin θ occurs at a half field angle of 45°. Although it is known that fsine-type distortion makes the brightness of the visual field uniform, if Ih/f is 0.707 or smaller, this means that distortion is too weak, thus making it difficult to achieve a wider angle.

On the other hand, if Ih/f is 0.956 or larger, a wider angle can be achieved, but the brightness in the periphery is reduced when the distortion deviates from the above-described f sin θ type in a wide-angle area. Note that, if an extreme peripheral brightness of about 60% relative to the center is ensured, that optical system can be used. This is clear from the fact that the extreme peripheral brightness in the optical system of Example 12 in PTL 5 is calculated to be 61.9% relative to the center, for example. The maximum half field angle in an optical system for an ultrasmall endoscope is generally 60°, and, a condition for realizing this brightness at 60° is Ih/f<0.956. Next, a description thereof will be given below.

First, a so-called f sin θ lens that satisfies the above-described condition is known to be an optical system for making the brightness uniform. Furthermore, a so-called fθ lens is known to be an optical system that can observe objects placed at an equal distance without any distortion. An optical system that can realize these two points is the best for users, and both lenses have completely identical configurations in a narrow-angle area where θ is small. This is because the rates of change with respect to θ of both lenses agree in the area where θ is small.

Figure 26:
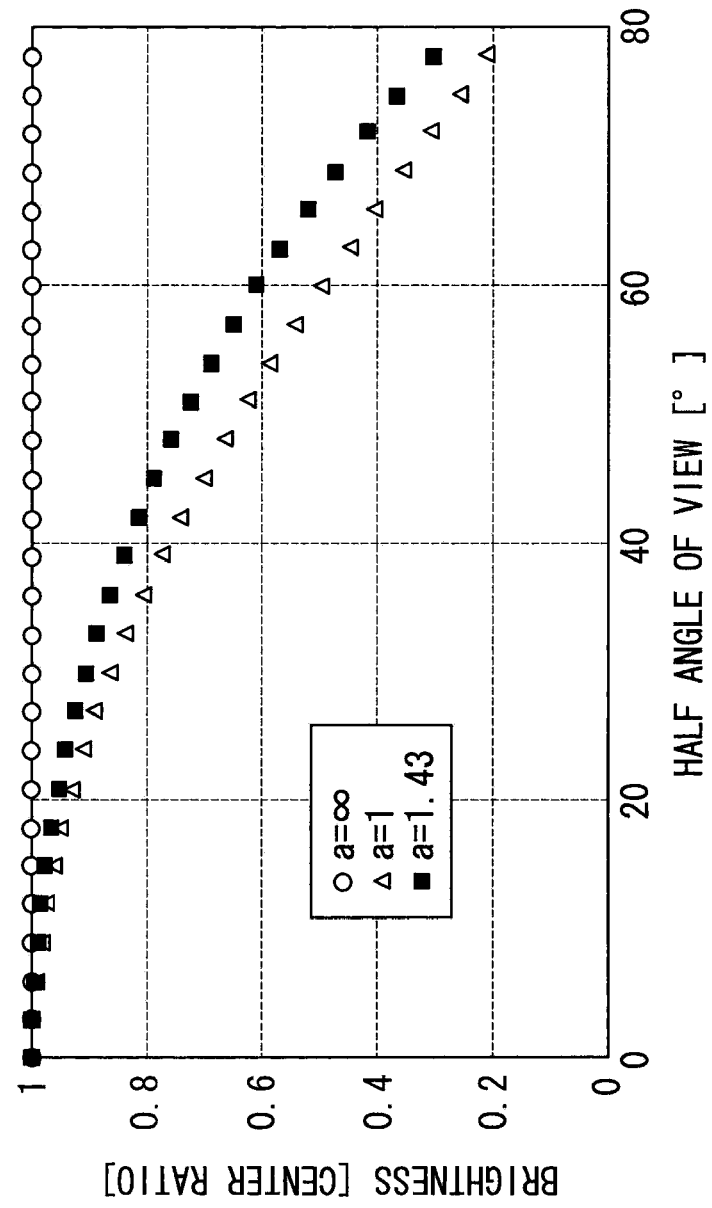
FIG. 26 is a view showing the relationship between the occurrence of distortion at half field angles and ambient brightness.

Thus, these are generalized to be expressed as αf sin(θ/α) by using a constant α. When α is equal to 1, αf sin(θ/α) corresponds to the f sin θ lens, and, when α is equal to ∞, αf sin(θ/α) corresponds to the fθ lens. This should be regarded as a scale expressing how close the shapes approximate their distortions. Thus, α for realizing a brightness of 60% relative to the center when θ is 60° is calculated to be 1.43 from FIG. 26, and, using this value, Ih/f is 0.956 when θ is 60°. From this point, when the distortion is increased to significantly deviate from the f sin θ type, the periphery becomes dark, thus reducing the merit of realizing a wide angle. Furthermore, because the chromatic aberration of magnification significantly appears as the field angle is increased, a sufficient resolving power in the periphery cannot be obtained when the half field angle exceeds 60°.

Conditional Expression (5) expresses a condition that can sufficiently inhibit the occurrence of flare caused when the chief ray strikes a portion of the frame between the front group GF and the rear group GR. If the ray height at the surface of the rear group GR that is closest to the object, with respect to the outermost off-axis ray that can be incident, is lower than the outer diameters of the lenses in the rear group GR, even if a ray enters from outside the visual field, flare caused when the ray strikes the inner circumferential surface of the portion of the frame between the front group GF and the rear group GR does not occur.

Therefore, in this embodiment, it is more preferable that a light-blocking member for mechanically blocking light be not included, other than the aperture stop.

As described above, according to the this embodiment, a mechanical light-blocking member, such as a mask, for preventing reflection at the inner circumferential surface of the frame is not required, thereby eliminating the need to provide a step structure for fixing the frame shape and the mechanical light-blocking member, which can simplify the structure of the frame. As a result, it is possible to achieve cost reduction and also to improve the ease-of-assembly because such a light-blocking member is not required to be built into or attached to the frame, whose area is small.

Figure 25:
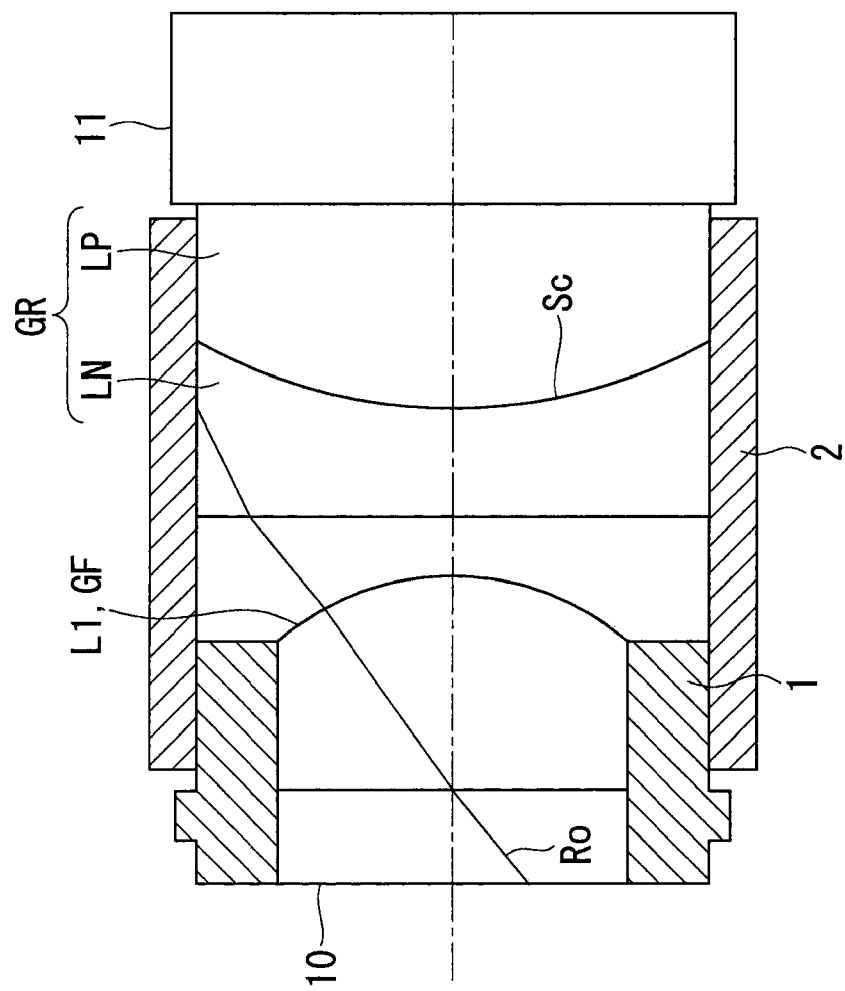
FIG. 25 is a view showing the path of an off-axis ray passing through the endoscope objective optical system shown in FIG. 1 and explaining a suppressive effect on the occurrence of flare at the inner circumferential surface of the frame.

As explained above, when Conditional Expression (1) is satisfied, the positive lens L1 is reduced in diameter. When Conditional Expression (2) is satisfied, it is possible to realize excellent incidence characteristics and ease-of-processing of the single lenses LP and LN. When Conditional Expression (3) is satisfied, the entire length can be reduced. When Conditional Expression (4) is satisfied, a wide angle can be achieved, which is suitable for use in an ultrathin endoscope. When Conditional Expression (5) is satisfied, even if an outermost off-axis chief ray Ro enters the optical system, the outermost off-axis chief ray Ro enters the single lens LN of the rear group GR, which is closer to the object, at a height of DR/2 or smaller, as shown in FIG. 25; therefore, the ray does not strike an inner circumferential surface of a frame 1 or 2, and thus flare is not caused by reflected light of the ray.

Therefore, the frames 1 and 2 do not require a mask or the like for cutting the flare light, thus eliminating the need to provide a step structure for fixing the mask or the like. Thus, as shown in FIG. 25, for example, with very simple structures of the frames 1 and 2, it is possible to provide a configuration in which, even if the outermost off-axis chief ray Ro enters the optical system, the outermost off-axis chief ray Ro is not reflected at the inner circumferential surface of the frame 1 or 2, thus eliminating the occurrence of flare.

In this embodiment, it is preferable that a light-blocking area for blocking light be formed on at least one of lens surfaces of the rear group through evaporation.

Of course it is preferable that side surfaces of the lenses in the rear group GR having positive refractive power, which the ray strikes, have structures for suppressing reflectance; for example, graining or black paint is applied to the side surfaces thereof. However, it is more preferable that a light-blocking area be formed through evaporation on at least one mirror surface of the lenses in the rear group GR, thus reducing the percentage of the area where rays strike. Specifically, the grained portion can also be formed to have a desired roughness or even to have a mirror surface, and black paint need not be applied. Therefore, the rear group GR can be formed of molded lenses, thereby making it possible to achieve a greater cost reduction and more stable quality.

EXAMPLES

Next, Examples of the above-descried objective optical system 100 according to the embodiment of the present invention will be described with reference to FIGS. 2 to 23. In the following Examples, the unit is mm, and the focal length is normalized to 1. F/# represents the f-number of the objective optical system, and W represents a half field angle. Furthermore, in surface data, r indicates the radius of curvature, d indicates an inter-surface distance, ne indicates a refractive index with respect to the e-line, ve indicates the Abbe number with respect to the e-line, and D/2 indicates the radius of the lens.

Example 1

Figure 2:
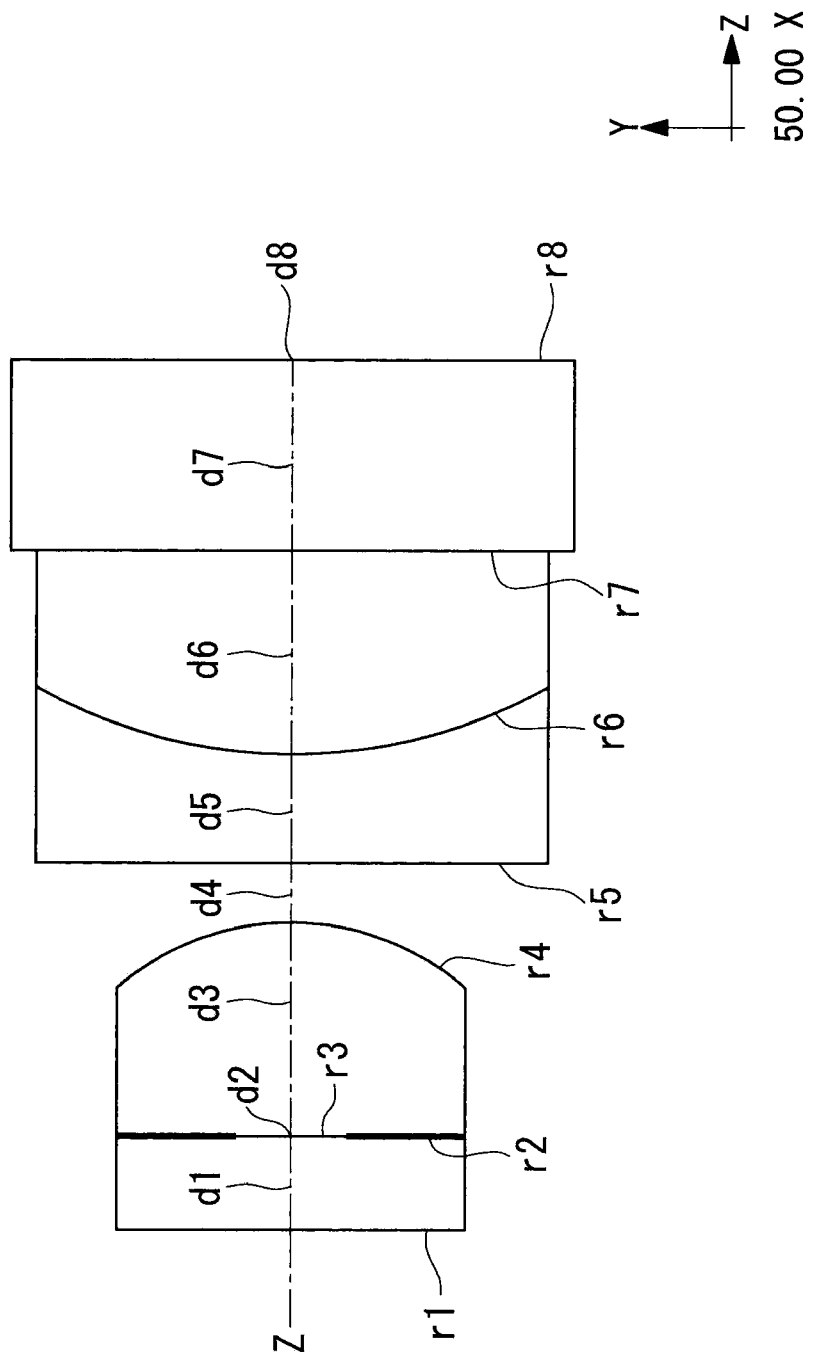
FIG. 2 is a lens cross-sectional view showing the configuration of an endoscope objective optical system according to Example 1 of the present invention.
Figure 3:
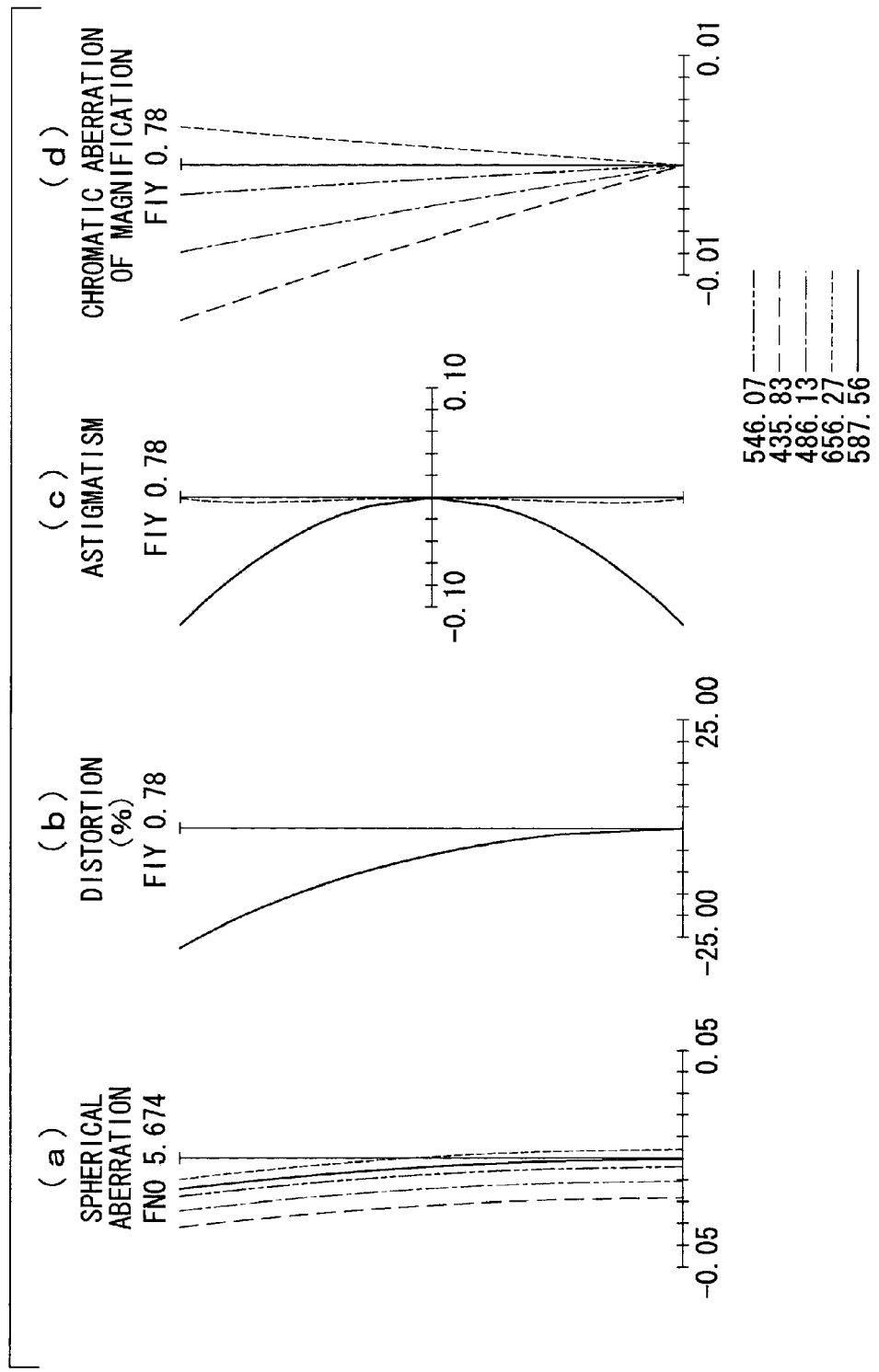
FIG. 3 includes aberration diagrams showing (a) spherical aberration, (b) distortion, (c) astigmatism, and (d) chromatic aberration of magnification of the endoscope objective optical system of Example 1.

As shown in FIG. 2, in an objective optical system according to Example 1 of the present invention, the aperture stop is formed on the cover glass through evaporation, the front group is formed of a single lens having a positive refractive index, and the rear group is formed of a joined lens consisting of, in order from the object side, a single lens having negative refractive power and a single lens having positive refractive power. In this Example, the single lens having negative refractive power in the rear group is formed into a meniscus shape. Various aberration diagrams of the objective optical system of this Example are shown in FIG. 3.

| Miscellaneous Data | | | | |
|---|---|---|---|---|
| F/5.674 | | | | |
| W = 46.11 | | | | |
| Ih = 40.778 | | | | |
| Hm = 40.642 | | | | |

| surface data | | | | | |
|---|---|---|---|---|---|
| Surface Number | r | d | ne | ve | D/2 |
| object plane | ∞ | 15.0000 | 1. | | |
| 1 | ∞ | 0.2937 | 1.51633 | 64.14 | 0.55 |
| 2 (aperture stop) | ∞ | 0. | 1. | | |
| 3 | ∞ | 0.6609 | 1.72916 | 54.68 | 0.55 |
| 4 | −0.8519 | 0.1832 | 1. | | |
| 5 | ∞ | 0.3378 | 1.51633 | 64.14 | 0.81 |
| 6 | 1.6611 | 0.6315 | 1.88300 | 40.76 | 0.81 |
| 7 | ∞ | 0.5875 | 1.52274 | 55.00 | 0.89 |
| 8 (image plane) | ∞ | 0. | | | |

Example 2

Figure 4:
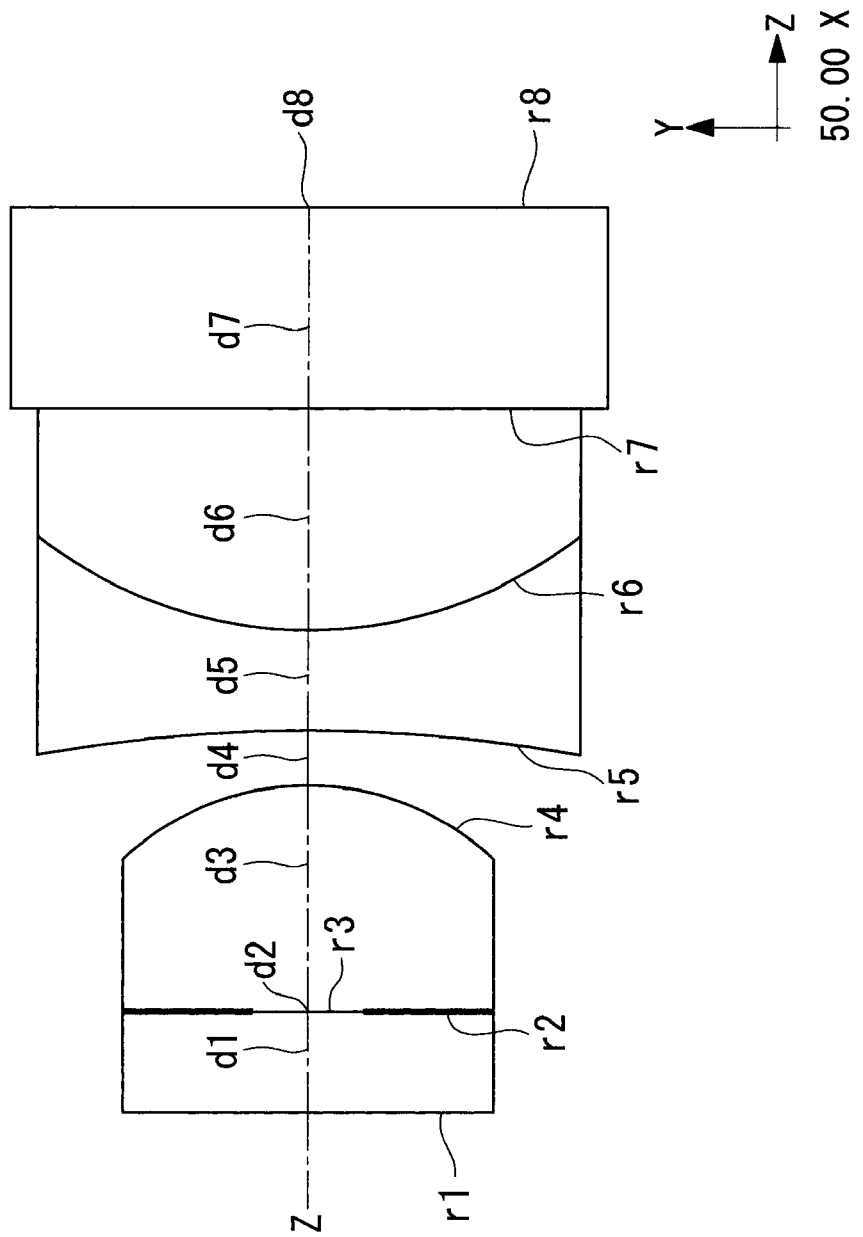
FIG. 4 is a lens cross-sectional view showing the configuration of an endoscope objective optical system according to Example 2 of the present invention.

As shown in FIG. 4, an objective optical system according to Example 2 of the present invention mainly differs from the objective optical system of Example 1 in that the single lens having negative refractive power in the rear group is formed into a biconcave shape. Various aberration diagrams of the objective optical system of this Example are shown in FIG. 5.

| Miscellaneous Data | | | | |
|---|---|---|---|---|
| F/5.353 | | | | |
| W = 451.91 | | | | |
| Ih = 40.825 | | | | |
| Hm = 40.619 | | | | |

| surface data | | | | | |
|---|---|---|---|---|---|
| Surface Number | r | d | ne | ve | D/2 |
| object plane | ∞ | 15.0000 | 1. | | |
| 1 | ∞ | 0.3114 | 1.51633 | 64.14 | 0.58 |
| 2 (aperture stop) | ∞ | 0. | 1. | | |
| 3 | ∞ | 0.7006 | 1.72916 | 54.68 | 0.58 |
| 4 | ∞ | 0.1713 | 1. | | |
| 5 | ∞ | 0.3114 | 1.52249 | 59.84 | 0.86 |
| 6 | ∞ | 0.6836 | 2.00330 | 28.27 | 0.86 |
| 7 | ∞ | 0.6227 | 1.52274 | 55.00 | 0.94 |
| 8 (image plane) | ∞ | 0. | | | |

Example 3

Figure 6:
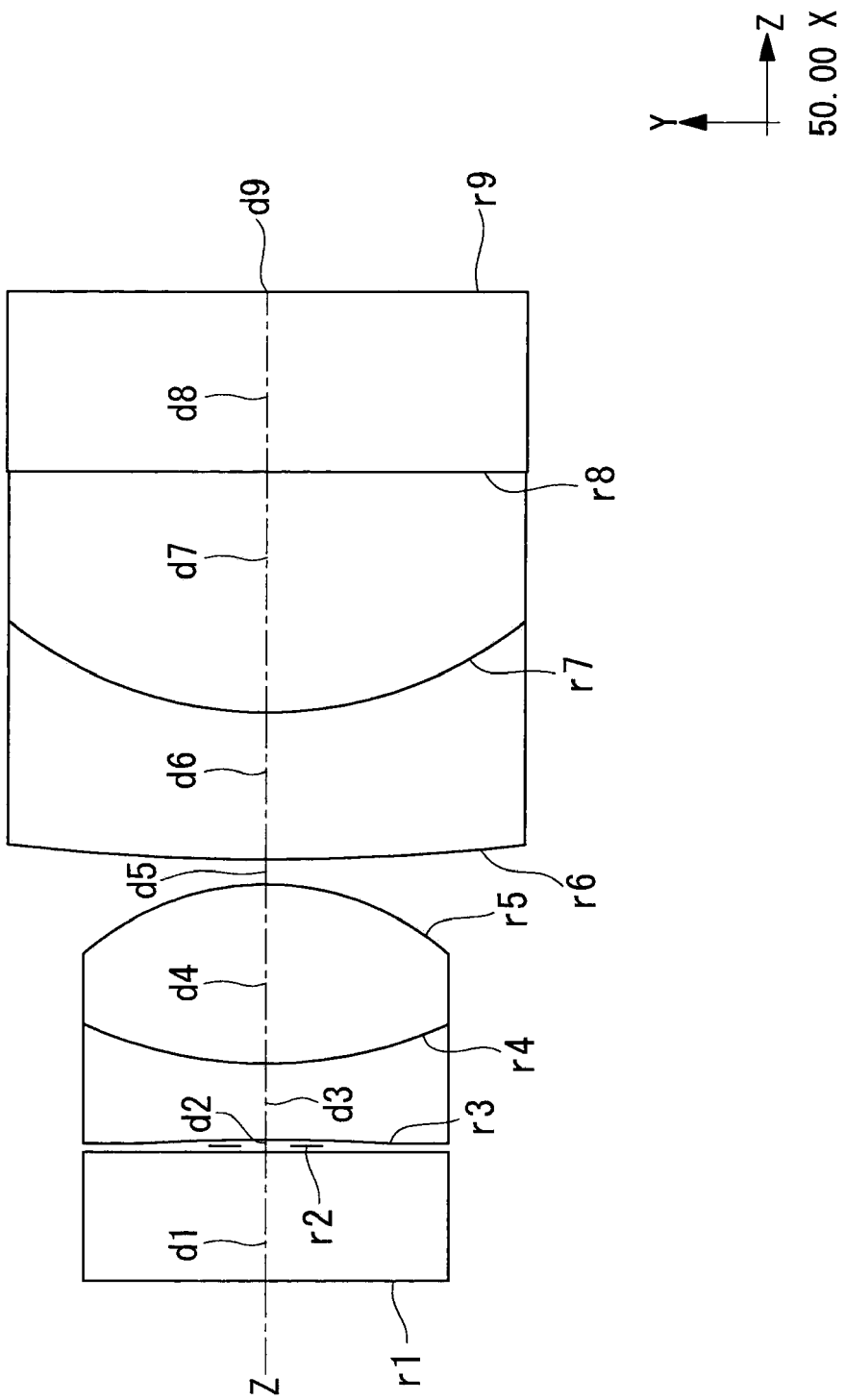
FIG. 6 is a lens cross-sectional view showing the configuration of an endoscope objective optical system according to Example 3 of the present invention.
Figure 7:
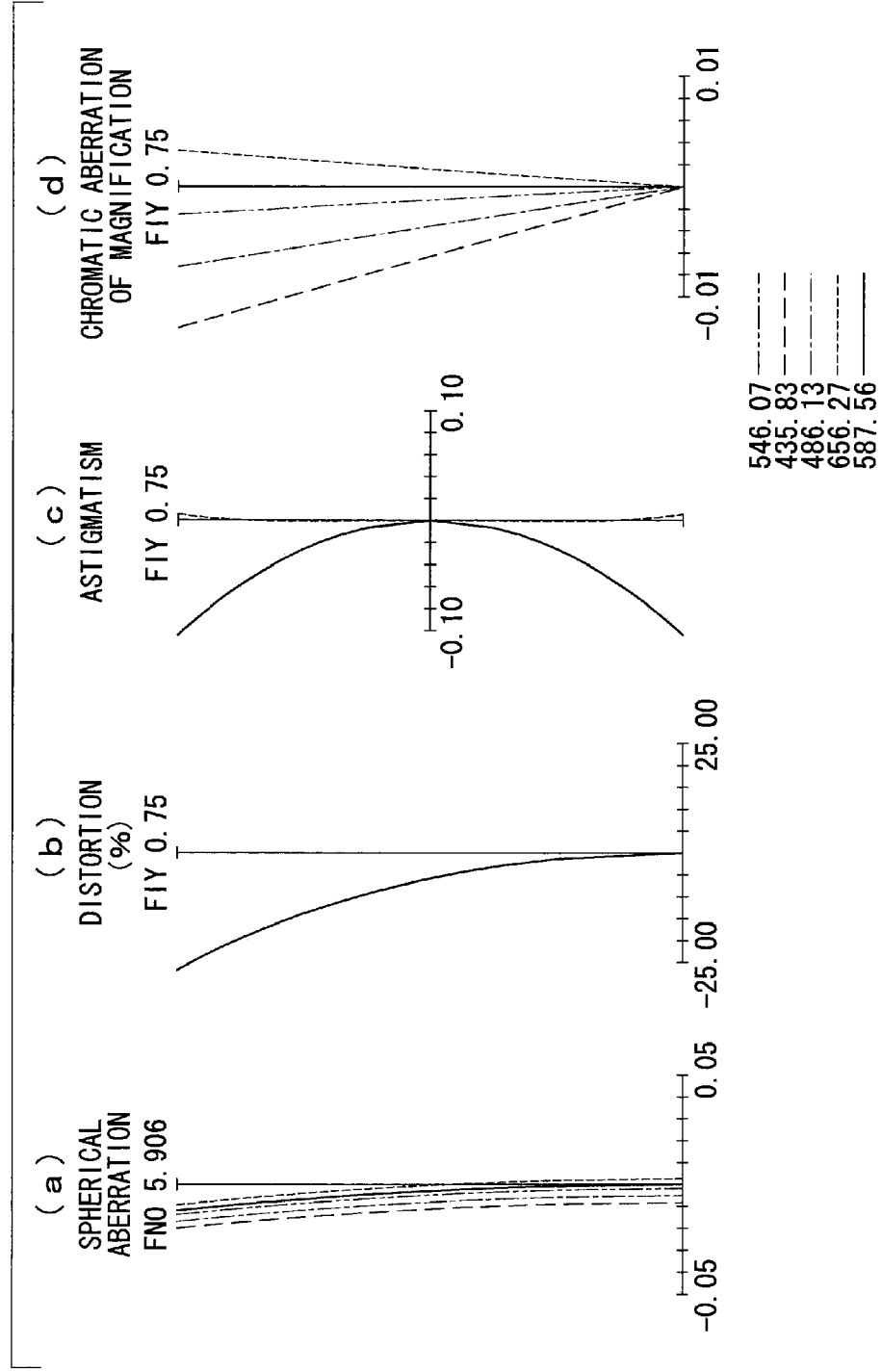
FIG. 7 includes aberration diagrams showing (a) spherical aberration, (b) distortion, (c) astigmatism, and (d) chromatic aberration of magnification of the endoscope objective optical system of Example 3.

As shown in FIG. 6, an objective optical system according to Example 3 of the present invention mainly differs from the objective optical system of Example 1 in that the aperture stop is formed separately from the cover glass and the lens, and the front group is formed of a joined lens. Various aberration diagrams of the objective optical system of this Example are shown in FIG. 7.

| Miscellaneous Data |
| --- |
| F/5.906 |
| W = 444.63 |
| Ih = 40.748 |
| Hm = 40.680 |

| surface data | | | | | |
| --- | --- | --- | --- | --- | --- |
| Surface Number | r | d | ne | ve | D/2 |
| object plane | ∞ | 10. | 1. | | |
| 1 | ∞ | 0.4147 | 1.88300 | 40.76 | 0.60 |
| 2 (aperture stop) | ∞ | 0.0400 | 1. | | |
| 3 | −7.1921 | 0.2445 | 1.66680 | 33.05 | 0.60 |
| 4 | 1.4607 | 0.5814 | 1.72916 | 54.68 | 0.60 |
| 5 | −0.9054 | 0.0787 | 1. | | |
| 6 | 7.4870 | 0.4728 | 1.51823 | 58.90 | 0.85 |
| 7 | 1.3748 | 0.7752 | 1.81600 | 46.62 | 0.85 |
| 8 | ∞ | 0.5783 | 1.52274 | 55.00 | 0.85 |
| 9 (image plane) | ∞ | 0. | | | |

Example 4

Figure 8:
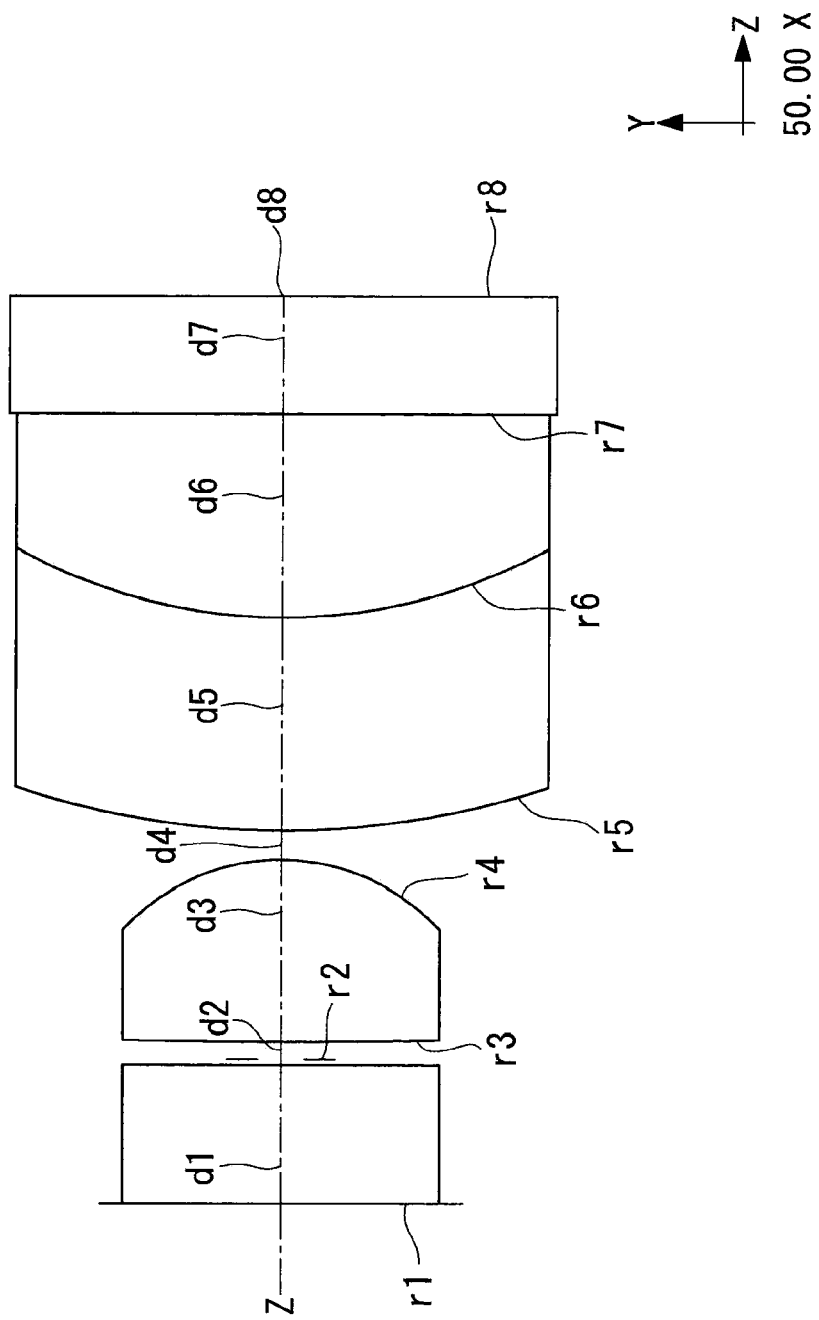
FIG. 8 is a lens cross-sectional view showing the configuration of an endoscope objective optical system according to Example 4 of the present invention.
Figure 9:
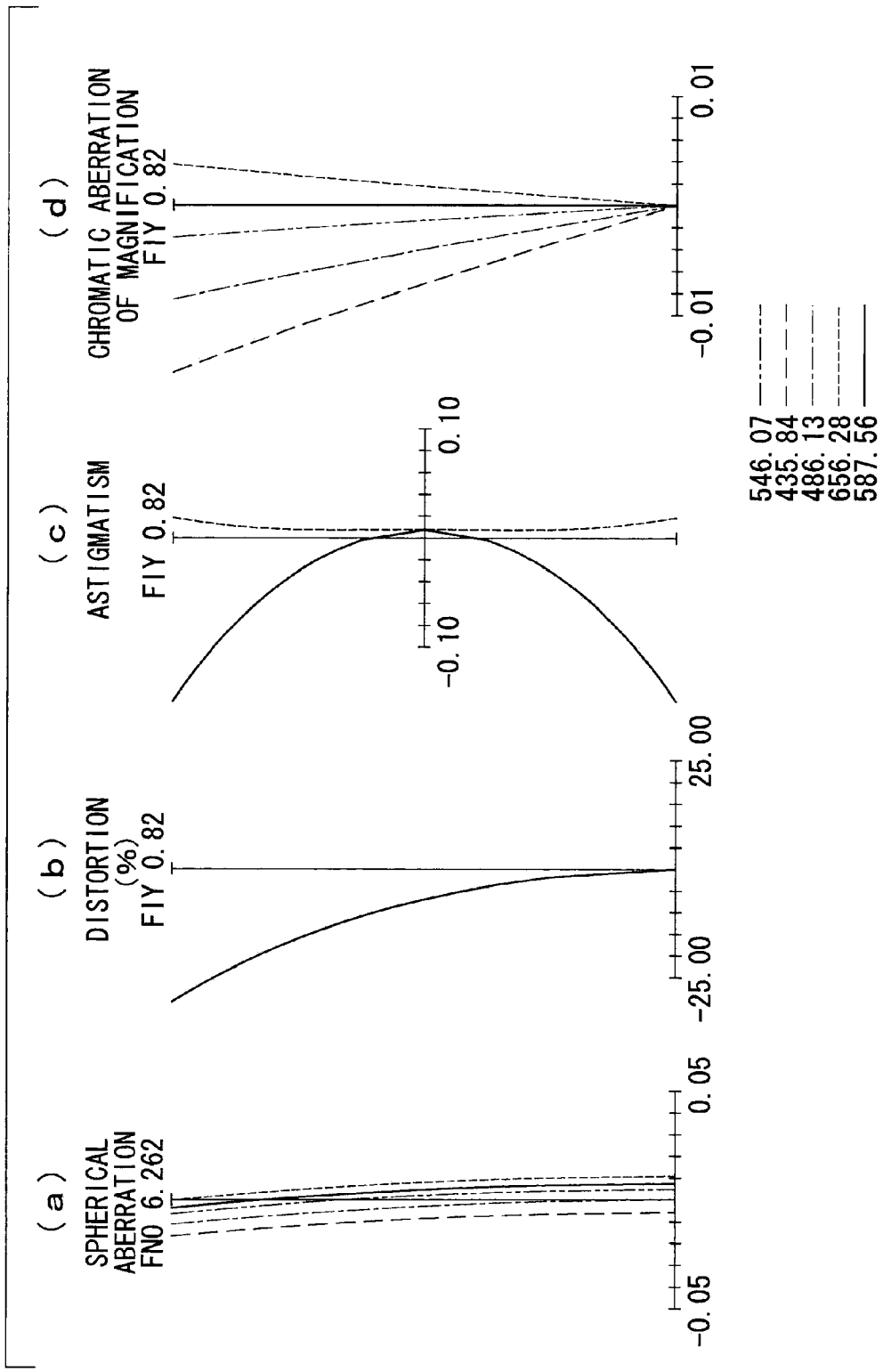
FIG. 9 includes aberration diagrams showing (a) spherical aberration, (b) distortion, (c) astigmatism, and (d) chromatic aberration of magnification of the endoscope objective optical system of Example 4.

As shown in FIG. 8, an objective optical system according to Example 4 of the present invention mainly differs from the objective optical system of Example 1 in that the aperture stop is formed separately from the cover glass and the lens and is located away from the front group. Such a configuration is useful, for example, in a case in which a sapphire substrate is used as the cover glass, which is located at the front end, and this substrate is metalized. Various aberration diagrams of the objective optical system of this Example are shown in FIG. 9.

| Miscellaneous Data |
| --- |
| F/6.262 |
| W = 48.73 |
| Ih = 0.820 |
| Hm = 0.550 |

| surface data | | | | | |
| --- | --- | --- | --- | --- | --- |
| Surface Number | r | d | ne | ve | D/2 |
| object plane | ∞ | 10. | 1. | | |
| 1 | ∞ | 0.4556 | 1.88300 | 40.76 | 0.53 |
| 2 (aperture stop) | ∞ | 0.0772 | 1. | | |
| 3 | 23.2095 | 0.5982 | 1.51633 | 64.14 | 0.53 |
| 4 | −0.7230 | 0.0965 | 1. | | |
| 5 | 2.8634 | 0.7043 | 1.59270 | 35.31 | 0.89 |
| 6 | 1.8814 | 0.6657 | 1.88300 | 40.76 | 0.89 |
| 7 | ∞ | 0.3859 | 1.51633 | 64.14 | 0.92 |
| 8 (image plane) | ∞ | 0. | | | |

Example 5

Figure 10:
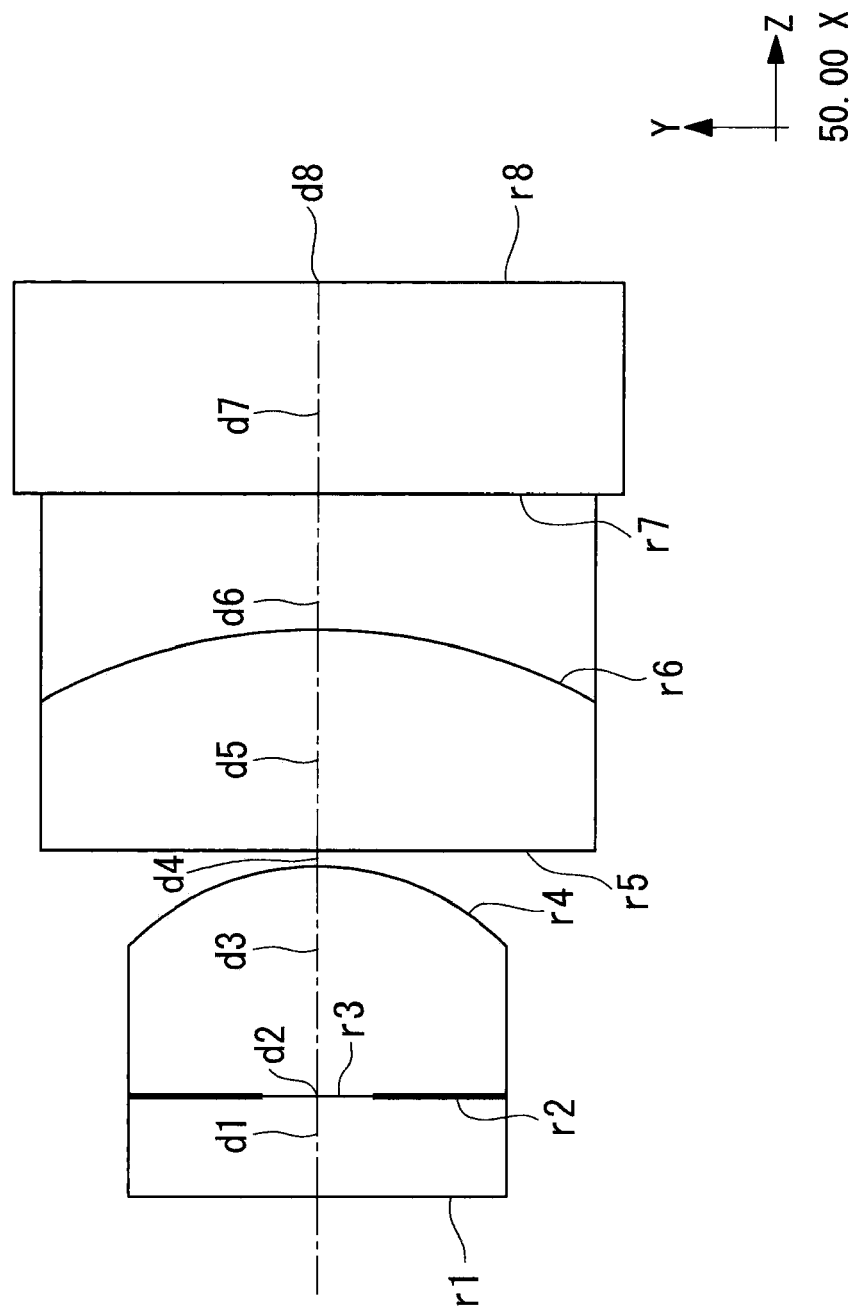
FIG. 10 is a lens cross-sectional view showing the configuration of an endoscope objective optical system according to Example 5 of the present invention.
Figure 11:
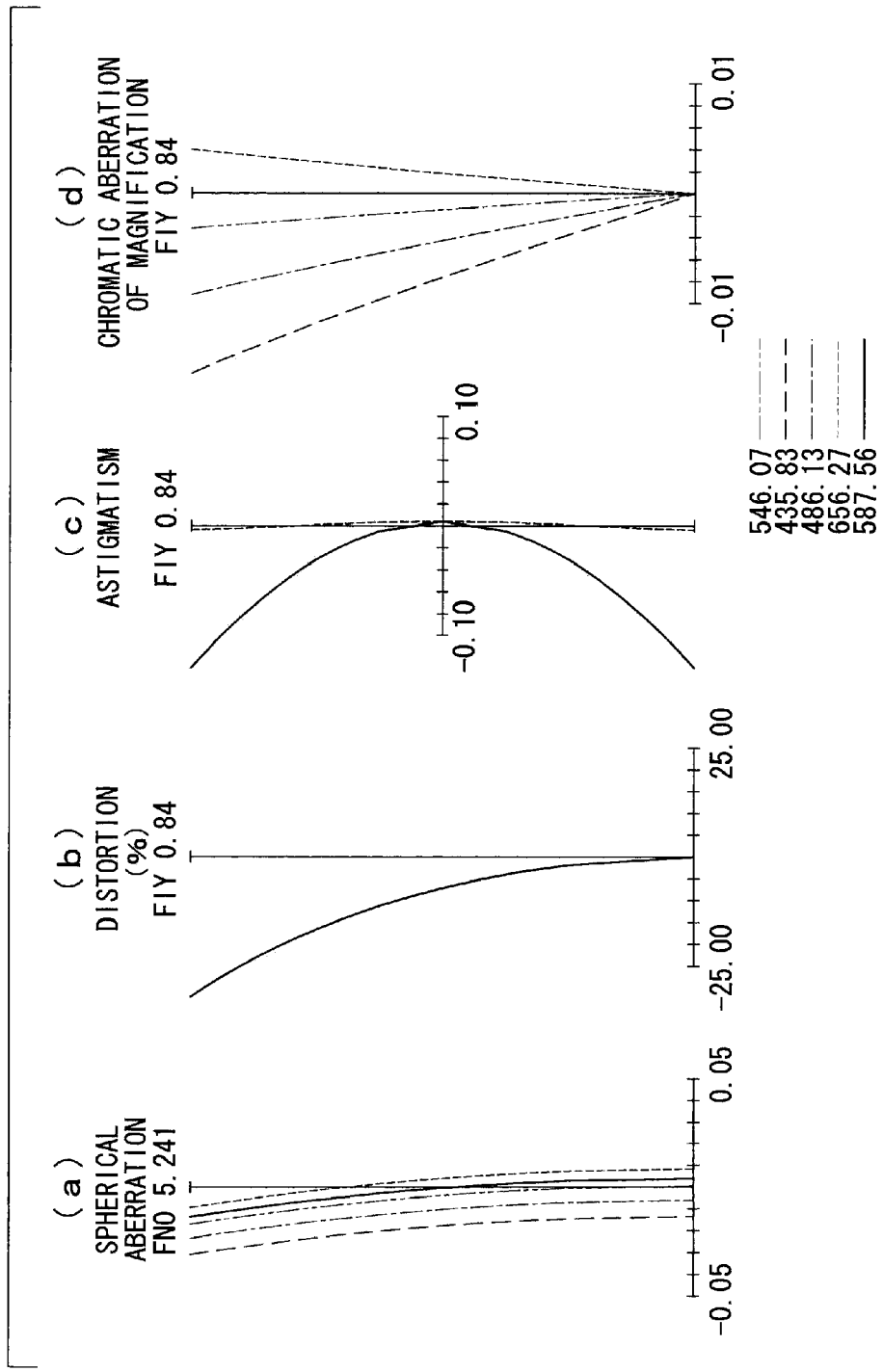
FIG. 11 includes aberration diagrams showing (a) spherical aberration, (b) distortion, (c) astigmatism, and (d) chromatic aberration of magnification of the endoscope objective optical system of Example 5.

As shown in FIG. 10, an objective optical system according to Example 5 of the present invention mainly differs from the objective optical system of Example 1 in that the rear group consists of, in order from the object side, a single lens having positive refractive power and a single lens having negative refractive power. In this Example, the single lens having positive refractive power is formed into a plano-convex shape. Furthermore, the aperture stop is formed on the cover glass through evaporation. Various aberration diagrams of the objective optical system of this Example are shown in FIG. 11.

| Miscellaneous Data |
| --- |
| F/5.241 |
| W = 50.29 |
| Ih = 0.843 |
| Hm = 0.556 |

| surface data | | | | | |
| --- | --- | --- | --- | --- | --- |
| Surface Number | r | d | ne | ve | D/2 |
| object plane | ∞ | 15.0000 | 1. | | |
| 1 | ∞ | 0.3110 | 1.51633 | 64.14 | 0.60 |
| 2 (aperture stop) | ∞ | 0. | 1. | | |
| 3 | ∞ | 0.7156 | 1.72916 | 54.68 | 0.60 |
| 4 | −0.8367 | 0.0477 | 1. | | |
| 5 | ∞ | 0.6838 | 1.88300 | 40.76 | 0.87 |
| 6 | −1.8316 | 0.4211 | 1.51633 | 64.14 | 0.87 |
| 7 | ∞ | 0.6522 | 1.52274 | 55.00 | 0.96 |
| 8 (image plane) | ∞ | 0. | | | |

Example 6

Figure 12:
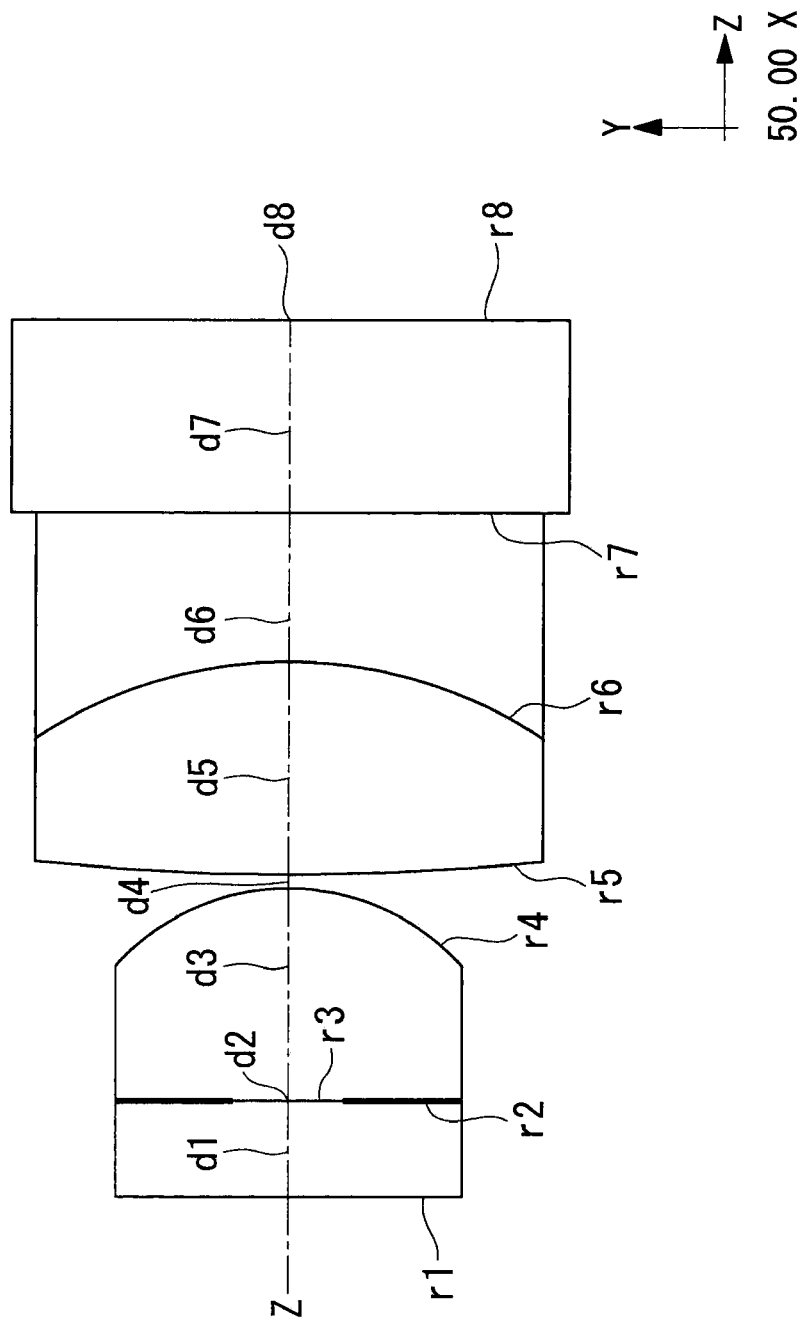
FIG. 12 is a lens cross-sectional view showing the configuration of an endoscope objective optical system according to Example 6 of the present invention.
Figure 13:
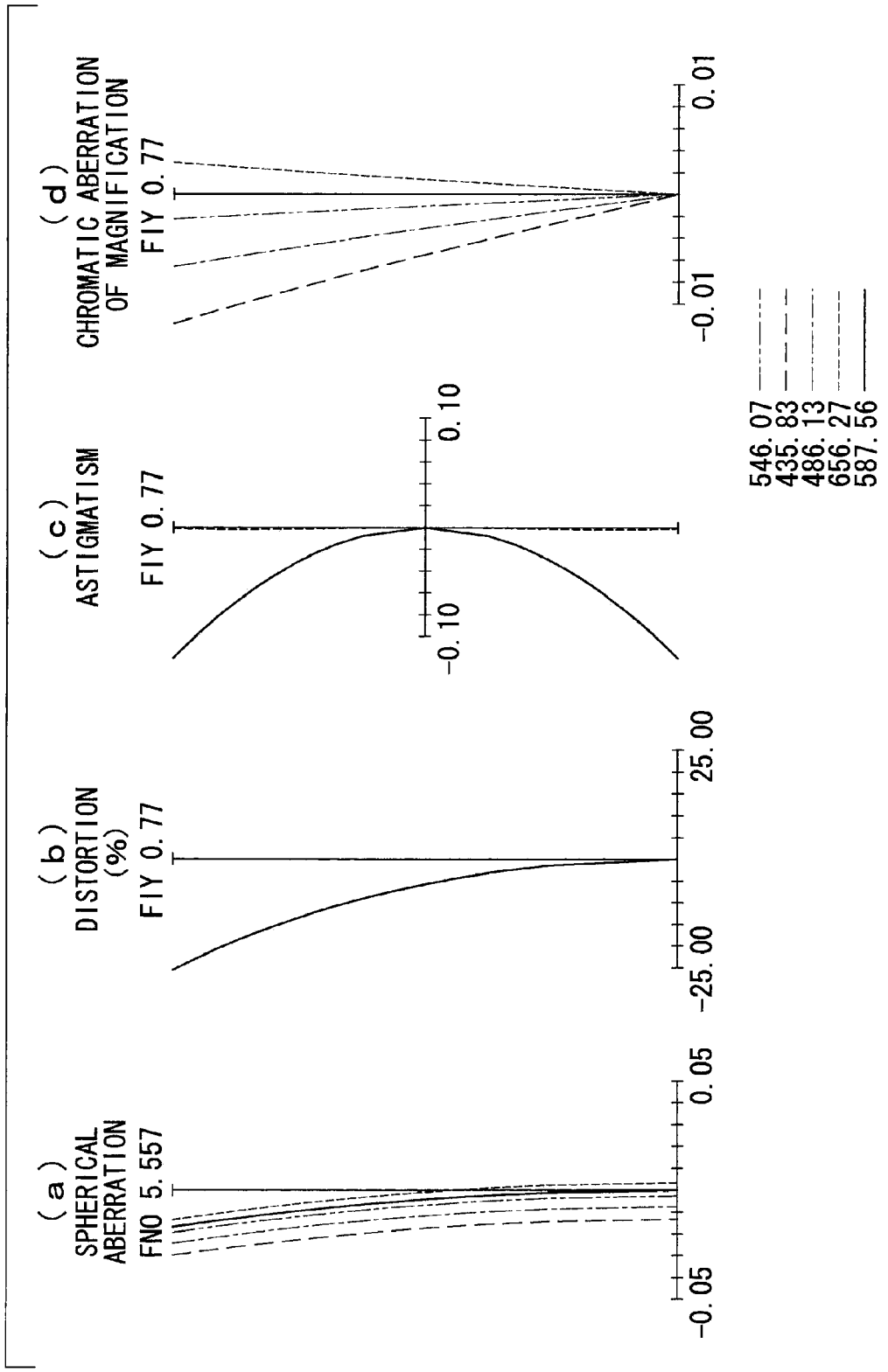
FIG. 13 includes aberration diagrams showing (a) spherical aberration, (b) distortion, (c) astigmatism, and (d) chromatic aberration of magnification of the endoscope objective optical system of Example 6.

As shown in FIG. 12, an objective optical system according to Example 6 of the present invention mainly differs from the objective optical system of Example 5 in that the single lens having positive refractive power in the rear group is formed into a biconvex shape. Various aberration diagrams of the objective optical system of this Example are shown in FIG. 13.

| Miscellaneous Data |
| --- |
| F/5.557 |
| W = 45.16 |
| Ih = 0.772 |
| Hm = 0.669 |

| surface data | | | | | |
| --- | --- | --- | --- | --- | --- |
| Surface Number | r | d | ne | ve | D/2 |
| object plane | ∞ | 15.0000 | 1. | | |
| 1 | ∞ | 0.2914 | 1.51633 | 64.14 | 0.55 |
| 2 (aperture stop) | ∞ | 0.0046 | 1. | | |
| 3 | ∞ | 0.6582 | 1.59522 | 67.74 | 0.55 |
| 4 | −0.7369 | 0.0437 | 1. | | |
| 5 | 8.0568 | 0.6611 | 1.75500 | 52.32 | 0.80 |
| 6 | −1.4682 | 0.4612 | 1.51633 | 64.14 | 0.80 |
| 7 | ∞ | 0.5944 | 1.52274 | 55.00 | 0.88 |
| 8 (image plane) | ∞ | 0. | | | |

Example 7

Figure 14:
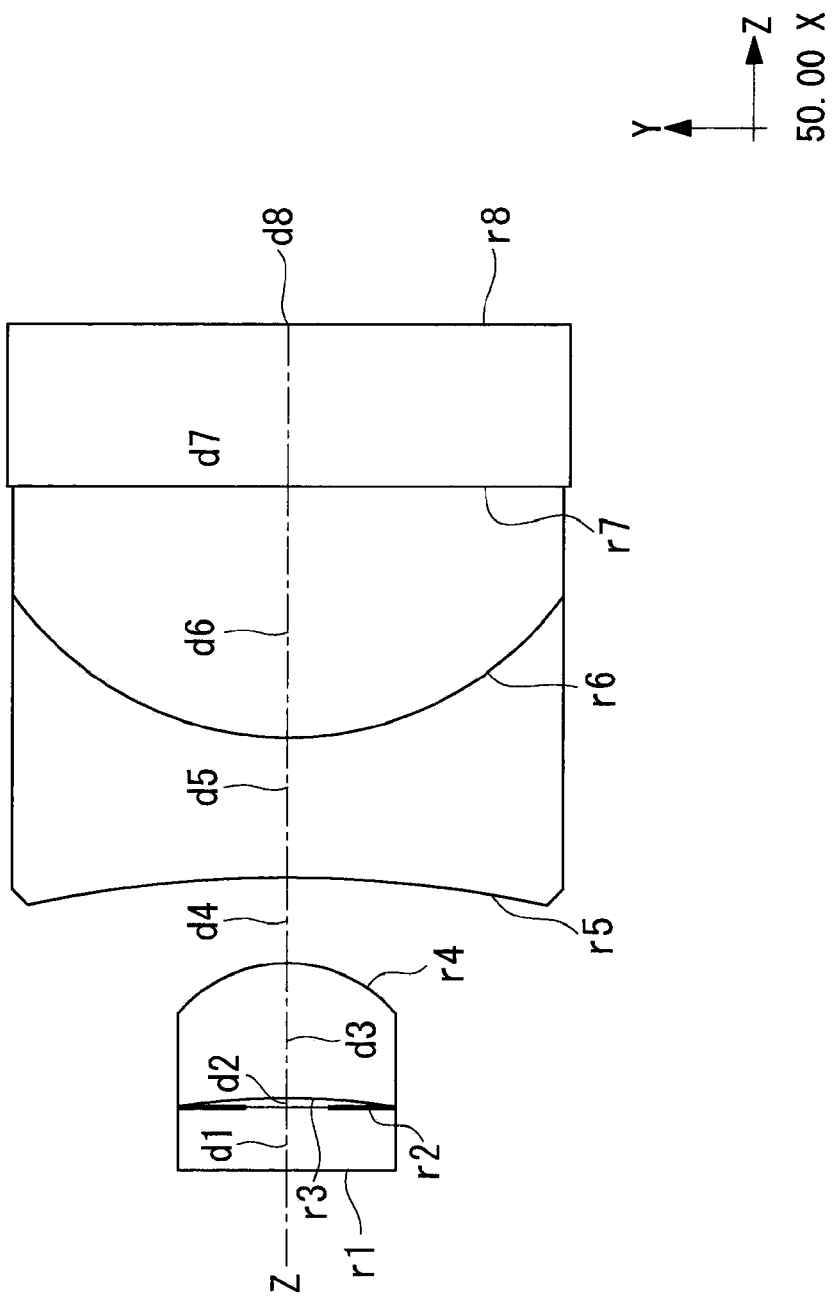
FIG. 14 is a lens cross-sectional view showing the configuration of an endoscope objective optical system according to Example 7 of the present invention.
Figure 15:
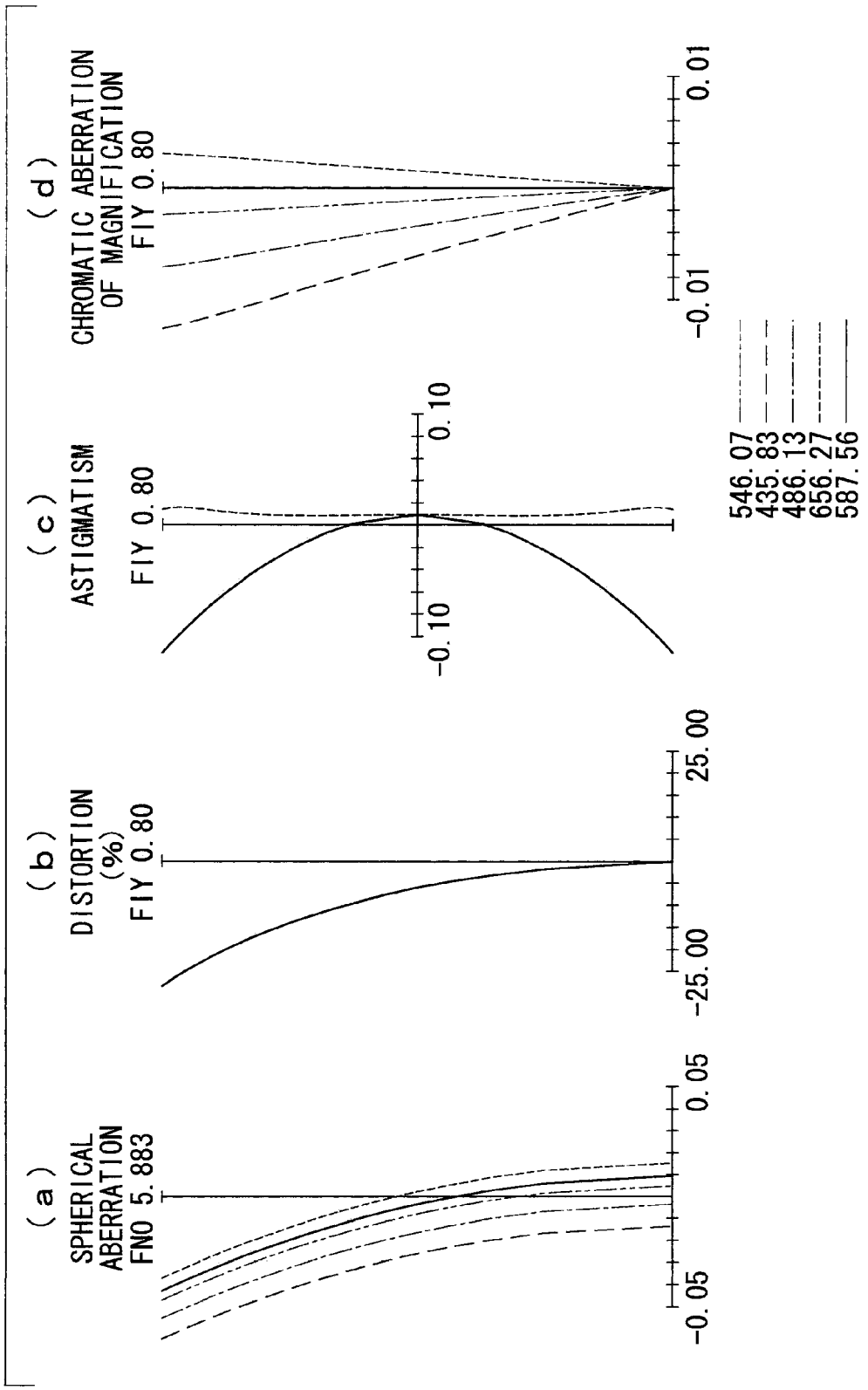
FIG. 15 includes aberration diagrams showing (a) spherical aberration, (b) distortion, (c) astigmatism, and (d) chromatic aberration of magnification of the endoscope objective optical system of Example 7.

As shown in FIG. 14, an objective optical system according to Example 7 of the present invention mainly differs from the objective optical system of Example 1 in that the difference in outer diameter between the front group and the rear group is large. Lenses in the rear group may be chamfered. Furthermore, when the rear group is painted in black or when an area for blocking rays is formed at a portion of the rear group through evaporation, the joining surface may be chamfered. In this Example, the aperture stop is also formed on the cover glass through evaporation. Various aberration diagrams of the objective optical system of this Example are shown in FIG. 15.

Miscellaneous Data

F/5.883
W = 45.13
Ih = 0.800
Hm = 0.647 surface data

| Surface Number | r | d | ne | ve | D/2 |
|---|---|---|---|---|---|
| object plane | ∞ | 5.0000 | 1. | | |
| 1 | ∞ | 0.2000 | 1.51633 | 64.14 | 0.35 |
| 2 (aperture stop) | ∞ | 0.0301 | 1. | | |
| 3 | −2.2136 | 0.4220 | 1.51633 | 64.14 | 0.35 |
| 4 | −0.4652 | 0.2686 | 1. | | |
| 5 | −4.0036 | 0.4389 | 1.51633 | 64.14 | 0.88 |
| 6 | 1.0884 | 0.7900 | 1.81600 | 46.62 | 0.88 |
| 7 | ∞ | 0.5072 | 1.49700 | 81.54 | 0.90 |
| 8 (image plane) | ∞ | 0. | | | |

Example 8

Figure 16:
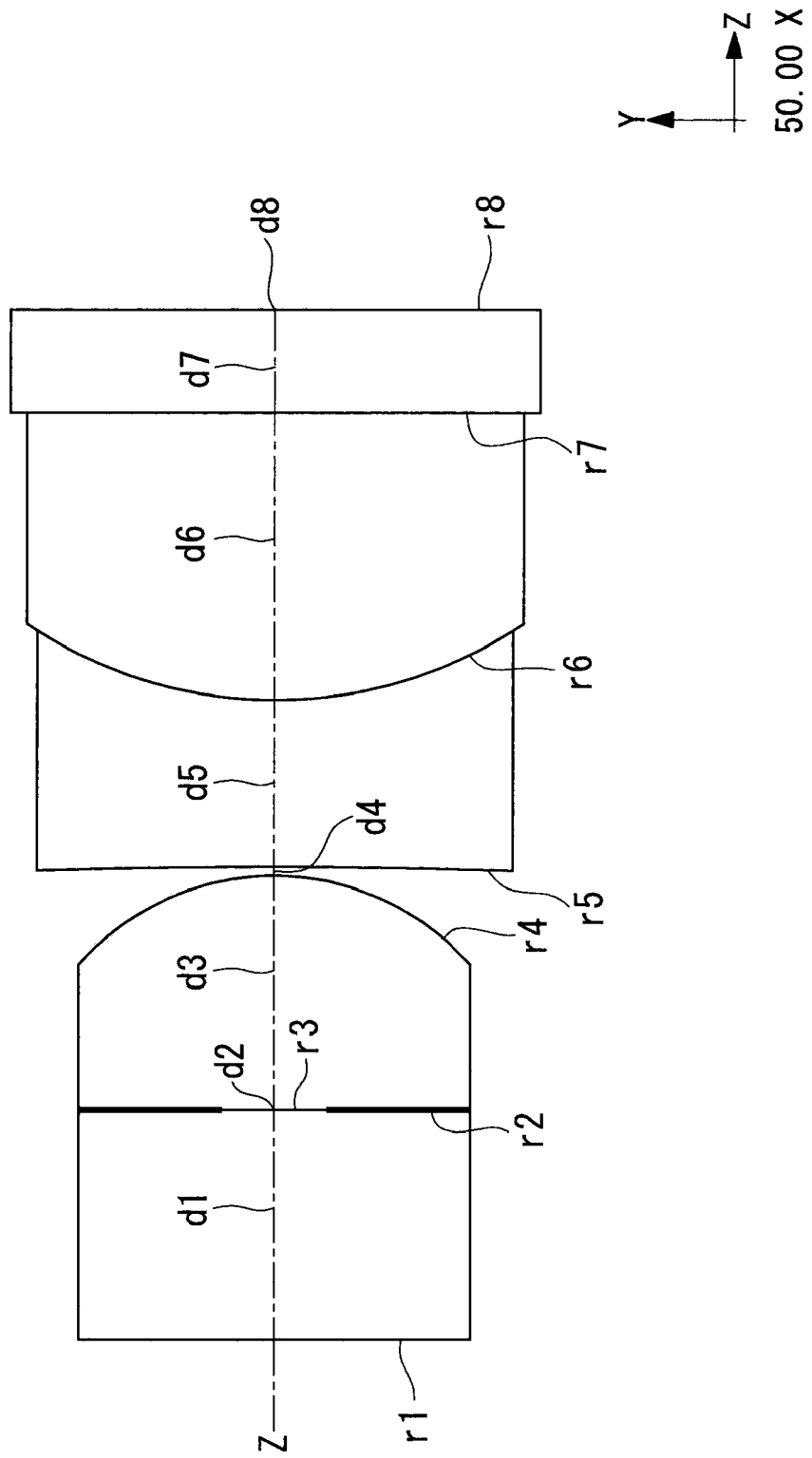
FIG. 16 is a lens cross-sectional view showing the configuration of an endoscope objective optical system according to Example 8 of the present invention.
Figure 17:
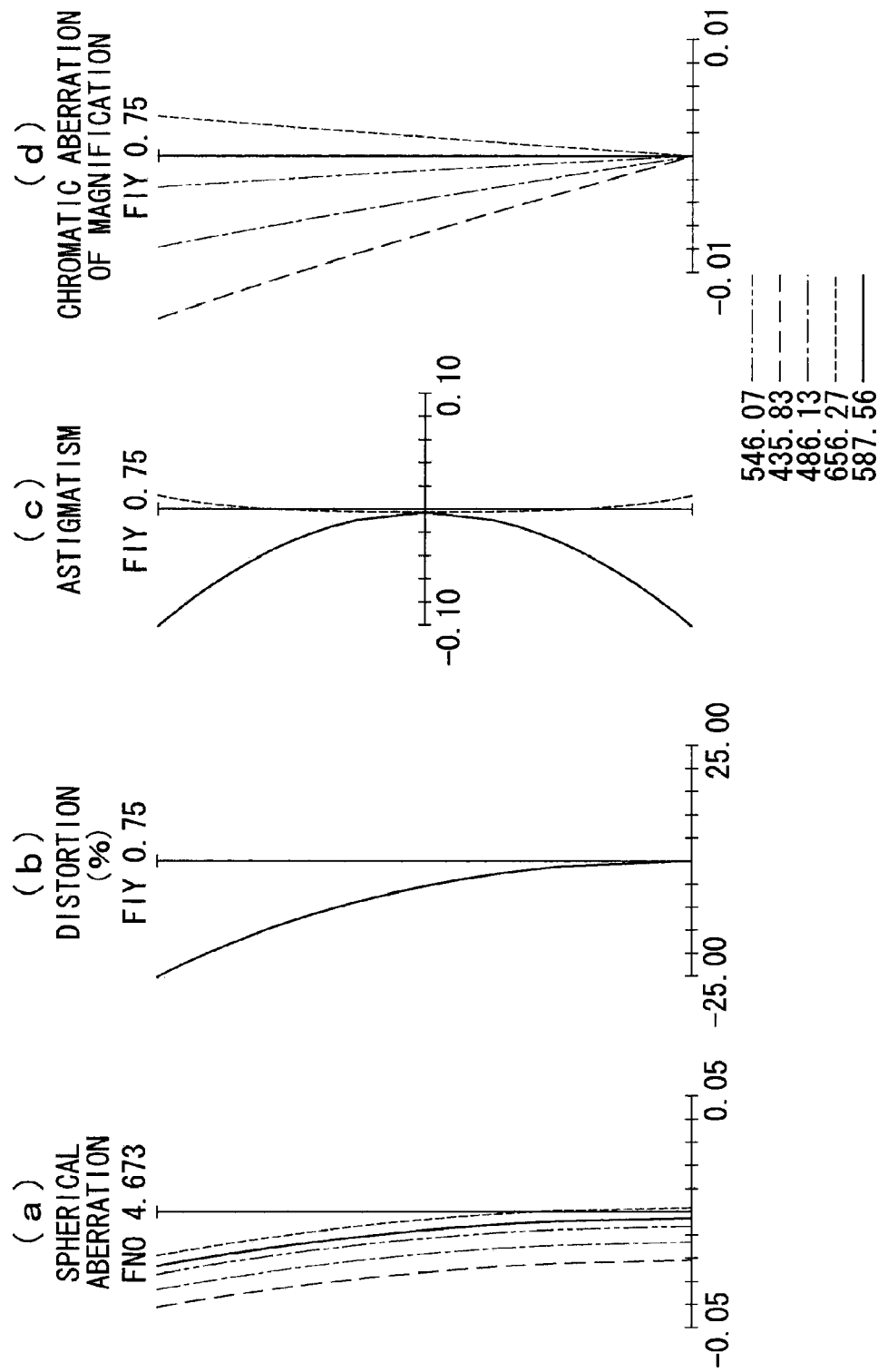
FIG. 17 includes aberration diagrams showing (a) spherical aberration, (b) distortion, (c) astigmatism, and (d) chromatic aberration of magnification of the endoscope objective optical system of Example 8.

As shown in FIG. 16, an objective optical system according to Example 8 of the present invention mainly differs from the objective optical system of Example 1 in that a thick glass is used as the cover glass. This cover glass can make it difficult for off-axis rays, which cause flare, to enter the objective optical system. In this Example, the single lens having positive refractive power and the single lens having negative refractive power in the rear group have outer diameters different from each other; however, when the area to be mated with the frame is required in order to ensure sufficient joining strength, it is preferable that these two single lenses have the same outer diameters. The aperture stop is formed on the cover glass through evaporation. Various aberration diagrams of the objective optical system of this Example are shown in FIG. 17.

Miscellaneous Data

F/4.673
W = 44.13
Ih = 0.745
Hm = 0.553 surface data

| Surface Number | r | d | ne | ve | D/2 |
|---|---|---|---|---|---|
| object plane | ∞ | 15.0000 | 1. | | |
| 1 | ∞ | 0.7476 | 1.88300 | 40.76 | 0.65 |
| 2 (aperture stop) | ∞ | 0. | 1. | | |
| 3 | ∞ | 0.7676 | 1.77250 | 49.60 | 0.65 |
| 4 | −0.8688 | 0.0290 | 1. | | |
| 5 | −23.4770 | 0.5420 | 1.51823 | 58.90 | 0.80 |
| 6 | 1.4954 | 0.9358 | 1.81600 | 46.62 | 0.83 |
| 7 | ∞ | 0.3336 | 1.52274 | 55.00 | 0.88 |
| 8 (image plane) | ∞ | 0. | | | |

Example 9

Figure 18:
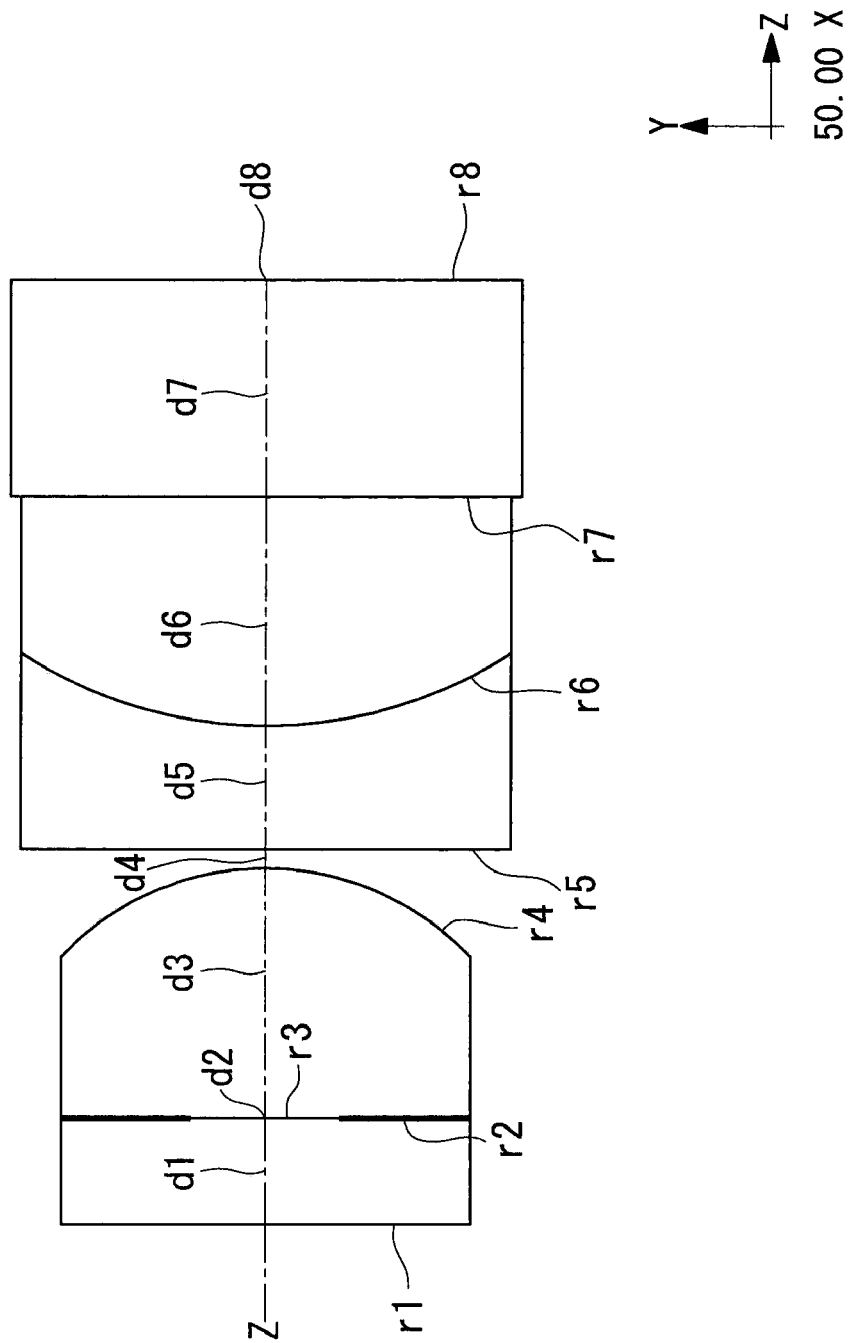
FIG. 18 is a lens cross-sectional view showing the configuration of an endoscope objective optical system according to Example 9 of the present invention.
Figure 19:
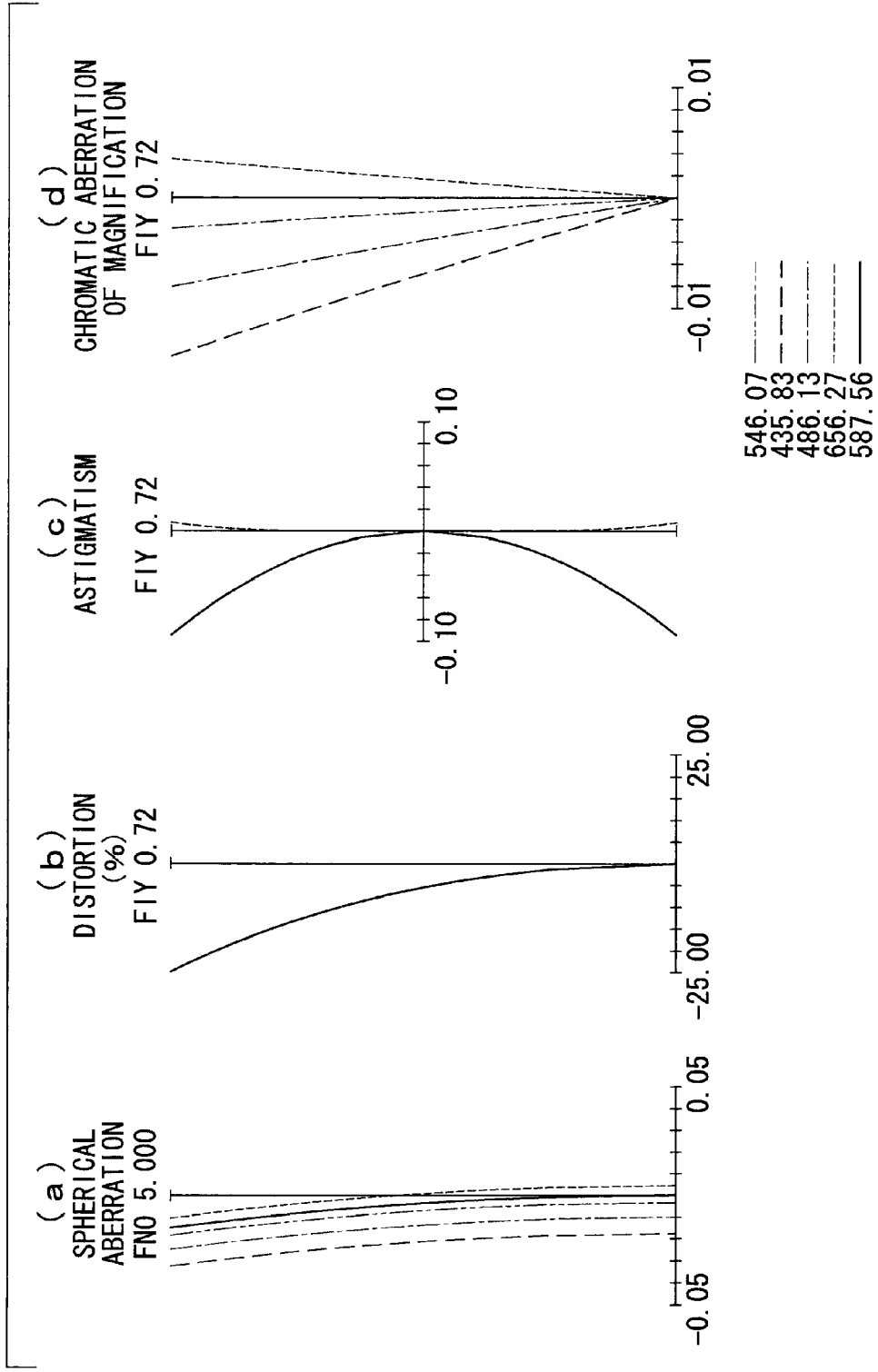
FIG. 19 includes aberration diagrams showing (a) spherical aberration, (b) distortion, (c) astigmatism, and (d) chromatic aberration of magnification of the endoscope objective optical system of Example 9.

As shown in FIG. 18, an objective optical system according to Example 9 of the present invention mainly differs from the objective optical systems of the other Examples in that sapphire is used as a glass material for the cover glass. With use of the cover glass made of sapphire in this way, the resistance to scratching and shocks can be improved. Furthermore, when the cover glass is metalized and fixed to the frame by soldering, it is possible to ensure water tightness and air tightness and also to enhance the fixing strength between the cover glass and the frame. Instead of sapphire, for example, a crystalline material, such as spinel or diamond, can be used as a glass material for the cover glass. Various aberration diagrams of the objective optical system of this Example are shown in FIG. 19.

Miscellaneous Data

F/5.000
W = 42.92
Ih = 0.720
Hm = 0.607 surface data

| Surface Number | r | d | ne | ve | D/2 |
|---|---|---|---|---|---|
| object plane | ∞ | 15.0000 | 1. | | |
| 1 | ∞ | 0.3316 | 1.76820 | 71.20 | 0.65 |
| 2 (aperture stop) | ∞ | 0. | 1. | | |
| 3 | ∞ | 0.7745 | 1.72916 | 54.68 | 0.65 |
| 4 | −0.8976 | 0.0589 | 1. | | |
| 5 | ∞ | 0.3824 | 1.52249 | 59.84 | 0.77 |
| 6 | 1.4371 | 0.7103 | 1.88300 | 40.76 | 0.77 |
| 7 | ∞ | 0.6681 | 1.52274 | 55.00 | 0.81 |
| 8 (image plane) | ∞ | 0. | | | |

Example 10

Figure 20:
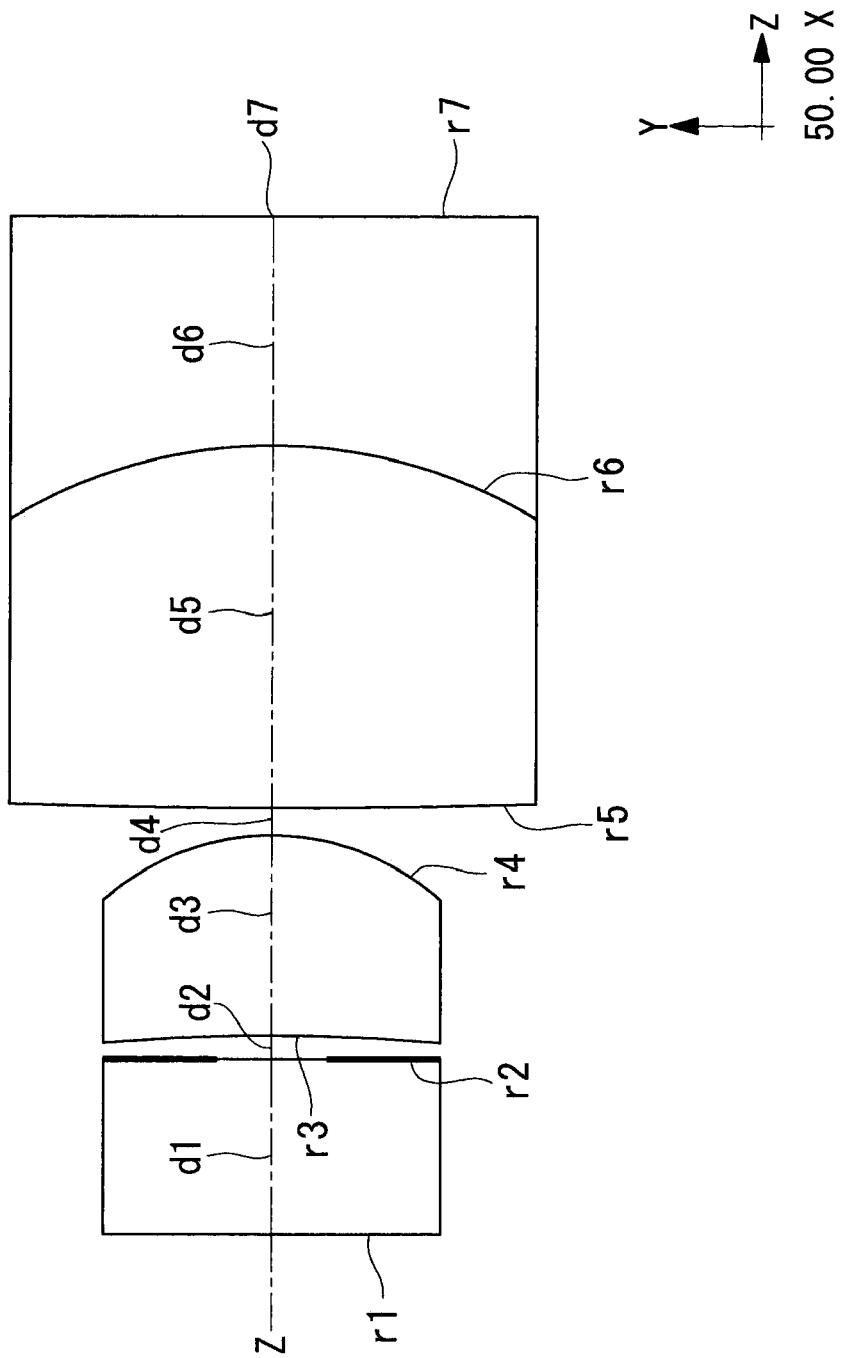
FIG. 20 is a lens cross-sectional view showing the configuration of an endoscope objective optical system according to Example 10 of the present invention.
Figure 21:
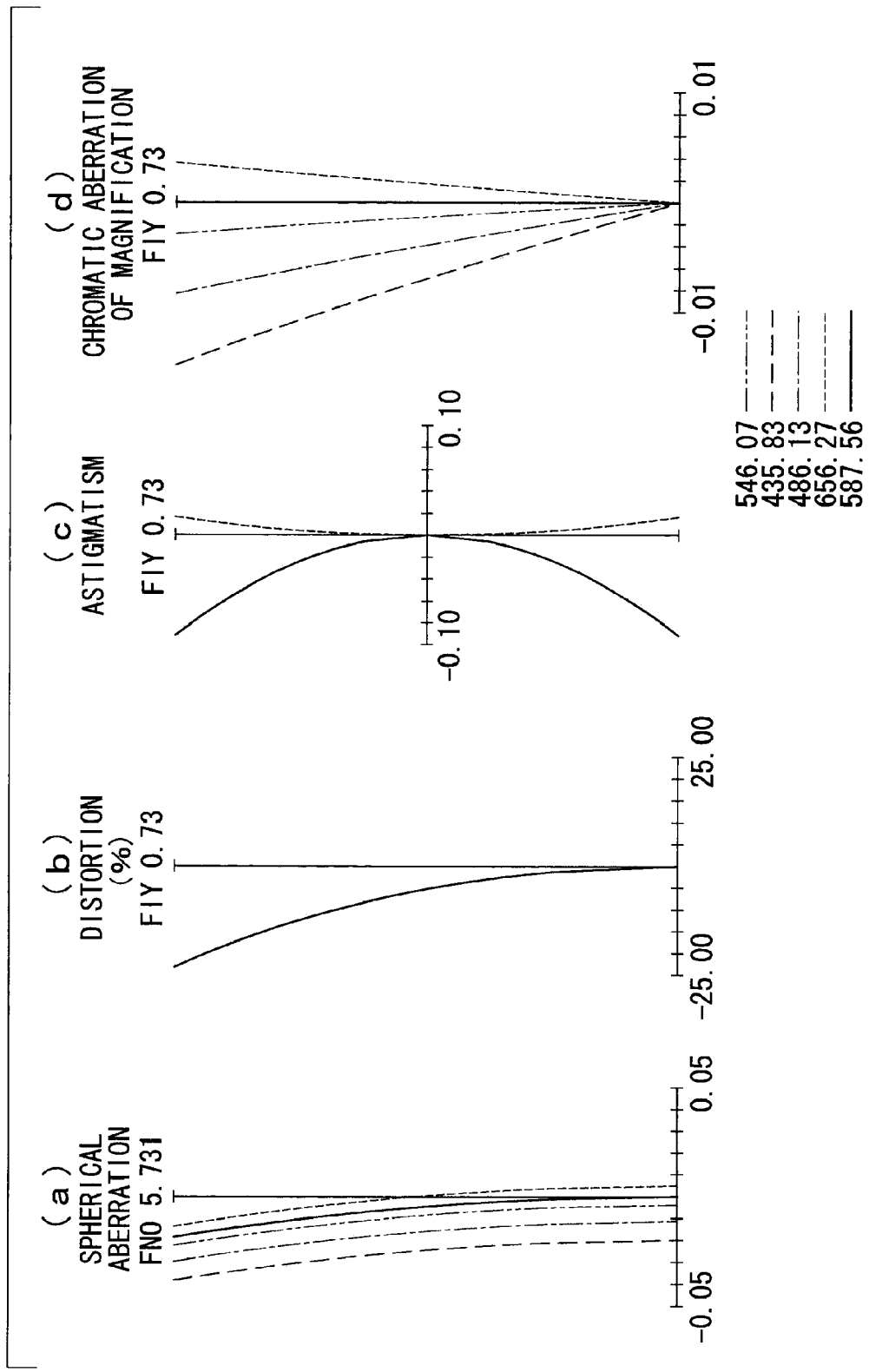
FIG. 21 includes aberration diagrams showing (a) spherical aberration, (b) distortion, (c) astigmatism, and (d) chromatic aberration of magnification of the endoscope objective optical system of Example 10.

As shown in FIG. 20, an objective optical system according to Example 10 of the present invention mainly differs from the objective optical systems of the other Examples in that the sealing glass, which is sandwiched between the rear group and an imaging lens, is omitted, and the lens of the rear group that is closer to an image is directly joined to a light receiving surface of the imaging device. Various aberration diagrams of the objective optical system of this Example are shown in FIG. 21.

Miscellaneous Data

F/5.731
W = 42.88
Ih = 0.720
Hm = 0.670 surface data

| Surface Number | r | d | ne | ve | D/2 |
|---|---|---|---|---|---|
| object plane | ∞ | 15.0000 | 1. | | |
| 1 | ∞ | 0.5401 | 1.88300 | 40.76 | 0.53 |
| 2 (aperture stop) | ∞ | 0.0748 | 1. | | |
| 3 | −5.9593 | 0.6232 | 1.78800 | 47.37 | 0.53 |
| 4 | −0.7988 | 0.0831 | 1. | | |
| 5 | 27.4705 | 1.1218 | 1.81600 | 46.62 | 0.83 |
| 6 | −1.6349 | 0.7079 | 1.52249 | 59.84 | 0.83 |
| 7 (image plane) | ∞ | 0. | | | |

Example 11

Figure 22:
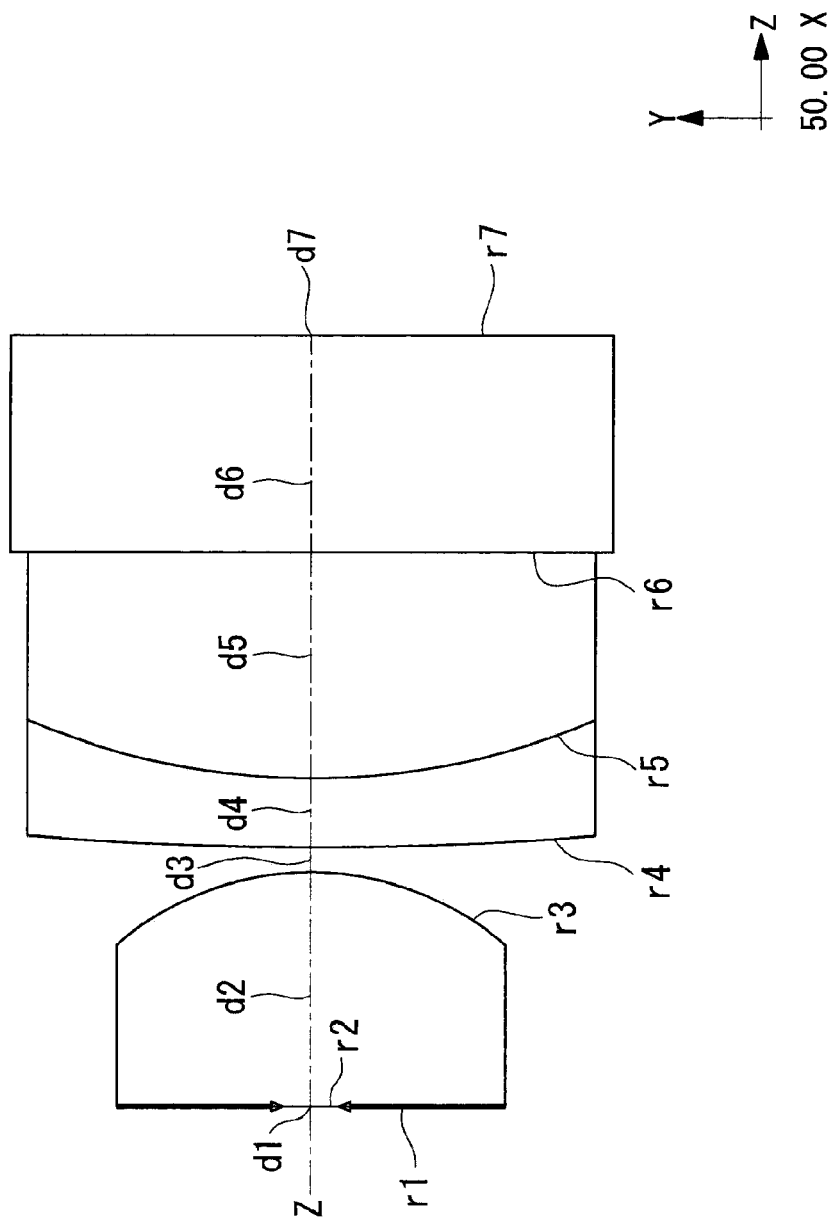
FIG. 22 is a lens cross-sectional view showing the configuration of an endoscope objective optical system according to Example 11 of the present invention.
Figure 23:
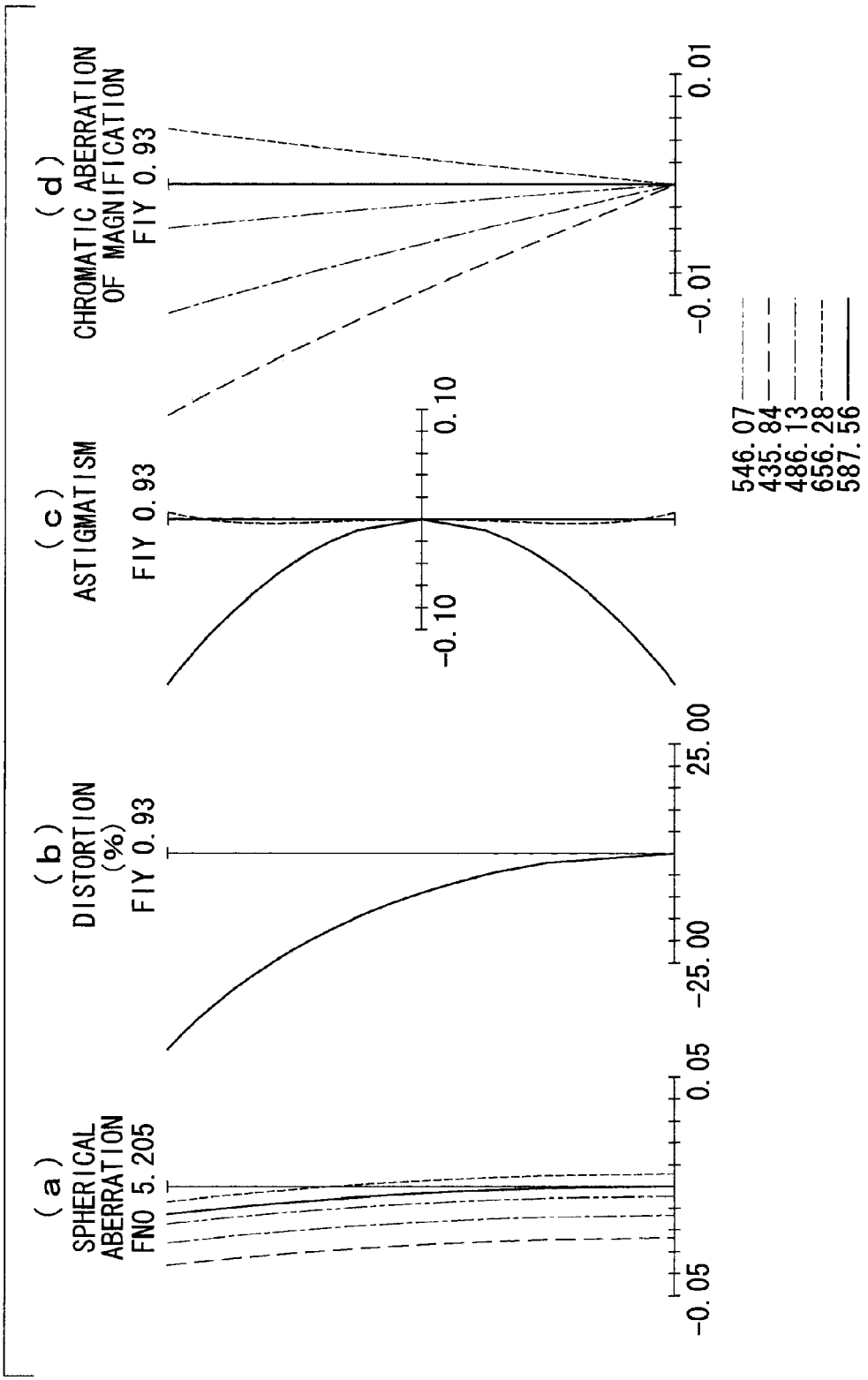
FIG. 23 includes aberration diagrams showing (a) spherical aberration, (b) distortion, (c) astigmatism, and (d) chromatic aberration of magnification of the endoscope objective optical system of Example 11.
Figure 24:
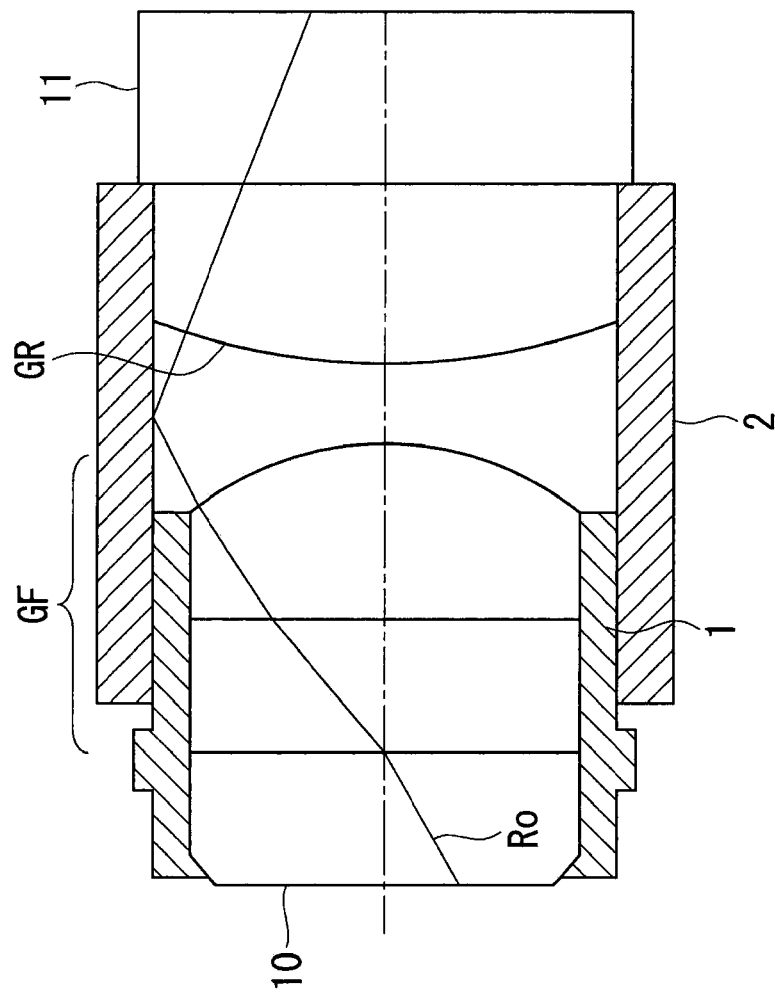
FIG. 24 is a view showing the configuration of a conventional endoscope objective optical system and the path of an off-axis ray when the ray is reflected at an inner circumferential surface of a frame, thus causing flare.

As shown in FIG. 22, an objective optical system according to Example 11 of the present invention mainly differs from the objective optical systems of the other Examples in that the cover glass, which is disposed at the front end, is omitted. In this case, if the aperture stop had a thickness, the lenses would be disposed at a distance set back from the front end of the endoscope, which would deteriorate the waterproofing properties. Therefore, it is desired that the surface of the front group that is closest to the object be flattened, and the aperture stop be formed on this flat surface through evaporation. Various aberration diagrams of the objective optical system of this Example are shown in FIG. 23.

| Miscellaneous Data |
| --- |
| F/5.205 |
| W = 58.3 |
| Ih = 0.931 |
| Hm = 0.593 |

| surface data | | | | | |
| --- | --- | --- | --- | --- | --- |
| Surface Number | r | d | ne | ve | D/2 |
| object plane | ∞ | 15.0000 | 1. | | |
| 1 (aperture stop) | ∞ | 0. | 1. | | |
| 2 | ∞ | 0.7934 | 1.88300 | 40.76 | 0.67 |
| 3 | −1.0415 | 0.0854 | 1. | | |
| 4 | 12.5738 | 0.2319 | 1.52249 | 59.84 | 0.98 |
| 5 | 2.5139 | 0.7685 | 1.88300 | 40.76 | 0.98 |
| 6 | ∞ | 0.7320 | 1.61380 | 49.90 | 1.04 |
| 7 (image plane) | ∞ | 0. | | | |

The values in Conditional Expressions (1) to (5) for the objective optical systems of Examples 1 to 11 are shown in Table 1.

TABLE 1

| Conditional expression | (1) fF/fR | (2) Φc · fR | (3) L/f | (4) Ih/f | (5) | |
| --- | --- | --- | --- | --- | --- | --- |
| | | | | | Hm | DR/2 |
| Example 1 | 0.257 | 1.000 | 2.695 | 0.778 | 0.642 | 0.81 |
| Example 2 | 0.286 | 1.408 | 2.801 | 0.825 | 0.619 | 0.86 |
| Example 3 | 0.361 | 0.769 | 3.193 | 0.749 | 0.680 | 0.85 |
| Example 4 | 0.475 | 0.452 | 2.983 | 0.820 | 0.780 | 0.89 |
| Example 5 | 0.230 | 1.000 | 2.831 | 0.843 | 0.556 | 0.87 |
| Example 6 | 0.310 | 0.649 | 2.715 | 0.772 | 0.669 | 0.80 |
| Example 7 | 0.165 | 1.758 | 2.657 | 0.800 | 0.647 | 0.88 |
| Example 8 | 0.201 | 1.115 | 3.356 | 0.745 | 0.553 | 0.83 |
| Example 9 | 0.309 | 1.000 | 2.926 | 0.720 | 0.607 | 0.73 |
| Example 10 | 0.229 | 0.872 | 3.151 | 0.731 | 0.670 | 0.83 |
| Example 11 | 0.217 | 0.779 | 2.611 | 0.931 | 0.593 | 0.98 |

REFERENCE SIGNS LIST

1, 2 frame
10 cover glass
11 sealing glass
100 endoscope objective optical system
AS aperture stop
GF front group
GR rear group
L1 positive lens
LN single lens having negative refractive power
LP single lens having positive refractive power
Ro outermost off-axis chief ray
Sc joining surface
Z optical axis

The invention claimed is:

1. An endoscope objective optical system consisting of: in order from an object side, an aperture stop; a front group having positive refractive power; and a rear group having positive refractive power,
   wherein the rear group is formed by joining a single lens having positive refractive power and a single lens having negative refractive power and is joined to an imaging device;
   a joining surface between the single lenses has positive refractive power; and
   the endoscope objective optical system satisfies following Conditional Expression (1):

$$0.15 < fF/fR < 0.5, \quad (1)$$

where fF indicates a focal length of the front group, and fR indicates a focal length of the rear group.

2. The endoscope objective optical system according to claim 1, wherein the following Conditional Expression (2) is satisfied:

$$0.4 < \phi c \cdot fR < 1.8, \quad (2)$$

where φc indicates a refractive power of the joining surface.

3. The endoscope objective optical system according to claim 1, wherein the following Conditional Expression (3) is satisfied:

$$2.0 < L/f < 3.4, \quad (3)$$

where f indicates a focal length of an entire system, and L indicates an entire length from a front end to a rear end of the entire system.

4. The endoscope objective optical system according to claim 1, wherein the following Conditional Expression (4) is satisfied:

$$0.707 < Ih/f < 0.956, \quad (4)$$

where Ih indicates a maximum image height on the imaging device.

5. The endoscope objective optical system according to claim 1, wherein the following Conditional Expression (5) is satisfied:

$$Hm < DR/2, \quad (5)$$

where Hm indicates a height of an outermost off-axis chief ray at a refractive surface of the rear group that is closest to an object, and DR indicates a maximum outer diameter of the lenses in the rear group.

6. The endoscope objective optical system according to claim 1, not comprising a light-blocking member for mechanically blocking light, other than the aperture stop.

7. The endoscope objective optical system according to claim 1, wherein a light-blocking area for blocking light is formed on at least one of lens surfaces of the rear group through evaporation.

8. An endoscope objective optical system consisting of: in order from an object side, a flat cover glass; an aperture stop; a front group having positive refractive power; and a rear group having positive refractive power,
   wherein the rear group is formed by joining a single lens having positive refractive power and a single lens having negative refractive power and is joined to an imaging device;
   a joining surface between the single lenses has positive refractive power; and
   the endoscope objective optical system satisfies following Conditional Expression (1):

$$0.15 < fF/fR < 0.5, \quad (1)$$

where fF indicates a focal length of the front group, and fR indicates a focal length of the rear group.

9. The endoscope objective optical system according to claim 8, wherein the following Conditional Expression (2) is satisfied:

$$0.4 < \phi c \cdot fR < 1.8, \quad (2)$$

where φc indicates a refractive power of the joining surface.

10. The endoscope objective optical system according to claim 8, wherein the following Conditional Expression (3) is satisfied:

$$2.0 < L/f < 3.4, \quad (3)$$

where f indicates a focal length of an entire system, and L indicates an entire length from a front end to a rear end of the entire system.

11. The endoscope objective optical system according to claim 8, wherein the following Conditional Expression (4) is satisfied:

$$0.707 < Ih/f < 0.956, \quad (4)$$

where Ih indicates a maximum image height on the imaging device.

12. The endoscope objective optical system according to claim 8, wherein the following Conditional Expression (5) is satisfied:

$$Hm < DR/2, \quad (5)$$

where Hm indicates a height of an outermost off-axis chief ray at a refractive surface of the rear group that is closest to an object, and DR indicates a maximum outer diameter of the lenses in the rear group.

13. The endoscope objective optical system according to claim 8, not comprising a light-blocking member for mechanically blocking light, other than the aperture stop.

14. The endoscope objective optical system according to claim 8, wherein a light-blocking area for blocking light is formed on at least one of lens surfaces of the rear group through evaporation.

* * * * *